United States Patent
Young et al.

(10) Patent No.: US 6,548,653 B1
(45) Date of Patent: Apr. 15, 2003

(54) ERYTHROPOIETIN ANALOG-HUMAN SERUM ALBUMIN FUSION

(75) Inventors: Michael Young, Weston, MA (US); Harry Meade, Newton, MA (US); Ian Krane, Westborough, MA (US)

(73) Assignee: Genzyme Transgenics Corporation, Framingham, MA (US)

( * ) Notice: Subject to any disclaimer, the term of this patent is extended or adjusted under 35 U.S.C. 154(b) by 0 days.

(21) Appl. No.: 09/333,213

(22) Filed: Jun. 15, 1999

Related U.S. Application Data

(60) Provisional application No. 60/089,343, filed on Jun. 15, 1998.

(51) Int. Cl.$^7$ .......................... C12N 5/00; C12P 21/04; C07H 21/04
(52) U.S. Cl. ...................... 536/23.4; 435/70.1; 435/325
(58) Field of Search .................... 800/7, 295; 435/325, 435/419, 254.2; 536/23.1, 23.4; 514/44

(56) References Cited

U.S. PATENT DOCUMENTS

| | | | |
|---|---|---|---|
| 4,703,008 A | 10/1987 | Lin | 435/240 |
| 4,970,300 A | 11/1990 | Fulton et al. | 530/383 |
| 5,441,868 A | 8/1995 | Lin | 435/69.4 |
| 5,547,089 A | 8/1996 | Daugherty, Jr. et al. | 213/62 R |
| 5,547,933 A | 8/1996 | Lin | 514/8 |
| 5,618,698 A | 4/1997 | Lin | 435/69.4 |
| 5,621,080 A | 4/1997 | Lin | 530/350 |
| 5,876,969 A | 3/1999 | Fleer et al. | 435/69.7 |

FOREIGN PATENT DOCUMENTS

| | | |
|---|---|---|
| EP | 0 314 317 A1 | 5/1989 |
| EP | 0 357 804 A1 | 3/1990 |
| EP | 0 370 205 B1 | 5/1990 |
| EP | 0 413 622 B1 | 2/1991 |
| EP | 0 427 189 | 5/1991 |
| EP | 0 428 267 B1 | 5/1991 |
| EP | 0 473 649 B1 | 3/1992 |
| JP | 3 201987 | 9/1991 |
| JP | 3201987 | 9/1991 |
| WO | WO 90/13653 | 11/1990 |
| WO | WO 93/15199 | 8/1993 |
| WO | WO 94/25055 | 11/1994 |
| WO | WO 95/05465 | 2/1995 |
| WO | WO 95/33057 | 12/1995 |
| WO | WO 96/19573 | 6/1996 |
| WO | WO 98/04718 | 2/1998 |

OTHER PUBLICATIONS

Bill, R. et al. Biochimica et Biophysica Acta 1340:13–20, Jun. 1997.*
Delorme, E. et al. Biochemistry 31:9871–9876, Oct. 1992.*
Higuchi, M. et al. The Journal of Biological Chemistry 267(111):7703–7709, Apr. 1992.*
Syed, S. et al. Blood 89(9):3243–3252, May 1997.*
Bill, R. et al. Biochimica et Biophysica Acta 1261:35–43, Mar. 1995.*
Korhonen, V. et al. European Journal of Biochemistry 245:482–489, Apr. 1997.*
Delorme et al.(1992) "Role of Glycosylation on the Secretion and Biological Activity of Erythropoeitin", *Biochemistry* 31:9871–9876.
International Search Report, Jan. 17, 2000.
R. Reed et al., *Clin. Chem.* vol. 34, No. 10, p. 1992–1994 (1988).
L.C. Walsley et al., *Blood*, vol. 77, No. 12, pp. 2624–2632 (1991).
K. Yamaguchi et al., *J. Biol. Chem.*, vol. 266, No. 30, pp. 20434–20439 (1991).
Broudy et al., "Recombinant Human Erythropoietin: Purification and Analysis of Carbohydrate Linkage," Archives of Biochemistry and Biophysics 265(No. 2): 329–336 (1988).
Hammarberg et al., "Dual affinity fusion approach and its use to express recombinant human insulin–like growth factor II," Proc. Natl. Acad. Sci. USA 86:4367–4371 (1989).
Lai et al., "Structural Characterization of Human Erythropoietin," The Journal of Biological Chemistry 261:3116–3121 (1986).
Lawn et al., "The sequence of human serum albumin cDNA and its expression in *E. coli*," Nucleic Acids Research 9 (No. 22): 6103–6114 (1981).
Minghetti et al., "Molecular Structure of the Human Albumin Gene Is Revealed by Nucleotide Sequence within q11–22 of Chromosome 4," The Journal of Biological Chemistry 261 (No. 15): 6747–6757 (1986).
Powell et al, "Human erythropoietin gene: High level expression in stably transfected mammalian cells and chromosome localization," Proc. Natl. Acad. Sci, USA 83: 6465–6469 (1986).

* cited by examiner

*Primary Examiner*—Deborah Crouch
*Assistant Examiner*—Joseph Woitach
(74) *Attorney, Agent, or Firm*—Fish & Richardson PC

(57) ABSTRACT

Erythropoietin analog-human serum albumin (EPOa-hSA) fusion protein and methods of making and using the fusion protein.

22 Claims, 2 Drawing Sheets

ERYTHROPOIETIN ANALOG-HUMAN SERUM ALBUMIN FUSION

This application claims the benefit of Provisional Application U.S. 60/089,343, filed Jun. 15, 1999.

BACKGROUND OF THE INVENTION

The invention relates to erythropoiein analog-human serum albumin (EPOa-hSA) fusion proteins, nucleic acids which encode EPOa-hSA fusion proteins, and methods of making and using EPOa-hSA fusion proteins and nucleic acids.

SUMMARY OF THE INVENTION

In general, the invention features, an EPOa-hSA fusion protein, wherein at least one amino acid residue of the EPOa moiety of the fusion protein is altered such that a site which serves as a site for glycosylation in erythropoietin (EPO) does not serve as a site for glycosylation in the EPOa, e.g., an EPOa-hSA fusion protein in which at least one amino acid residue which can serve as a glycosylation site in erythropoietin is altered, e.g., by substitution or deletion, such that it does not serve as a glycosylation site.

In a preferred embodiment, the EPOa-hSA fusion protein has the formula: R1-L-R2; R2-L-R1; or R1-L-R2-L-R1, wherein R1 is an EPOa amino acid sequence, L is a peptide linker and R2 is human serum albumin amino acid sequence. Preferably, R1 and R2 are covalently linked via the peptide linker.

In a preferred embodiment: an amino acid residue of EPO which serves as an attachment point for glycosylation has been deleted; an amino acid residue of EPO which serves as a site for glycosylation has been replaced with an amino acid residue which does not serve as a site for glycosylation; the amino acid residue which is altered is selected from the group consisting of amino acid residues Asn24, Asn38, Asn83 and Ser126; the glycosylation site at amino acid residue Ser126 and at least one additional N-linked glycosylation site selected from the group consisting of Asn24, Asn38 and Asn83 are altered; a glycosylation site which provides for N-linked glycosylation is altered by replacing an Asn residue with an amino acid residue other than it, e.g., Gln; a glycosylation site which provides for O-linked glycosylation is altered by replacing a Ser residue with an amino acid residue other than it, e.g., Ala.

In preferred embodiments, the EPOa-hSA fusion protein is made in a mammary gland of a transgenic mammal, e.g., a ruminant, e.g., a goat.

In preferred embodiments, the EPOa-hSA fusion protein is secreted into the milk of a transgenic mammal, e.g., a ruminant, e.g., a goat.

In preferred embodiments, the EPOa-hSA fusion protein is made, in a transgenic animal, under the control of a mammary gland specific promoter, e.g., a milk specific promoter, e.g., a milk serum protein or casein promoter. The milk specific promoter can be a casein promoter, beta lactoglobulin promoter, whey acid protein promoter, or lactalbumin promoter. Preferably, the promoter is a goat β casein promoter.

In preferred embodiments, the EPOa-hSA fusion protein, in a transgenic animal, and is secreted into the milk of a transgenic mammal at concentrations of at least about 0.2 mg/ml, 0.5 mg/ml, 0.75 mg/ml, 1 mg/ml, 2 mg/ml, 3 mg/ml or higher.

In a preferred embodiment, amino acid residue Asn24 has been altered, e.g., substituted or deleted. Preferably, the amino acid residue Asn24 has been replaced with Gln.

In a preferred embodiment, amino acid residue Asn38 has been altered, e.g., substituted or deleted. Preferably, amino acid residue Asn38 has been replaced with Gln.

In a preferred embodiment, amino acid residue Asn83 has been altered, e.g., substituted or deleted. Preferably, the amino acid residue Asn83 has been replaced with Gln.

In yet another embodiment, amino acid residue Ser126 has been altered, e.g., substituted or deleted. Preferably, the amino acid residue Ser126 has been replaced with Ala.

In a preferred embodiment: each of amino acid residue Asn24, Asn38, Asn83 and Ser126 has been altered, e.g., substituted or deleted, such that it does not serve as a glycosylation site; each of the amino acid residues Asn24, Asn28, Asn83 and Ser126 has, respectively, been replaced with Gln, Gln, Gln, and Ala.

In a preferred embodiment, the fusion protein includes a peptide linker and the peptide linker has one or more of the following characteristics: a) it allows for the rotation of the erythropoietin analog amino acid sequence and the human serum albumin amino acid sequence relative to each other; b) it is resistant to digestion by proteases; and c) it does not interact with the erythropoietin analog or the human serum albumin.

In a preferred embodiment: the fusion protein includes a peptide linker and the peptide linker is 5 to 60, more preferably, 10 to 30, amino acids in length; the peptide linker is 20 amino acids in length; the peptide linker is 17 amino acids in length; each of the amino acids in the peptide linker is selected from the group consisting of Gly, Ser, Asn, Thr and Ala; the peptide linker includes a Gly-Ser element.

In a preferred embodiment, the fusion protein includes a peptide linker and the peptide linker includes a sequence having the formula (Ser-Gly-Gly-Gly-Gly)$_y$ wherein y is 1, 2, 3, 4, 5, 6, 7, or 8. Preferably, the peptide linker includes a sequence having the formula (Ser-Gly-Gly-Gly-Gly)$_3$. Preferably, the peptide linker includes a sequence having the formula ((Ser-Gly-Gly-Gly-Gly)$_3$-Ser-Pro).

In a preferred embodiment, the fusion protein includes a peptide linker and the peptide linker includes a sequence having the formula (Ser-Ser-Ser-Ser-Gly)$_y$ wherein y is 1, 2, 3, 4, 5, 6, 7, or 8. Preferably, the peptide linker includes a sequence having the formula ((Ser-Ser-Ser-Ser-Gly)$_3$-Ser-Pro).

In another aspect, the invention features, an EPOa-hSA fusion protein wherein the EPOa includes amino acid residues Gln24, Gln38, Gln83 and Ala126.

In a preferred embodiment the EPOa is Gln24, Gln38, Gln83, Ala126 EPO (i.e., only amino acids 24, 38, 83, and 126 differ from wild type).

In another aspect, the invention features, an EPOa-hSA fusion protein which includes from left to right, an EPOa which includes amino acid residues Gln24, Gln38, Gln83 and Ala126, a peptide linker, e.g., a peptide linker having the formula ((Ser-Gly-Gly-Gly-Gly)$_3$-Ser-Pro), and human serum albumin.

In a preferred embodiment the EPOa is Gln24, Gln38, Gln83, Ala126 EPO.

In a preferred embodiment the fusion protein is from left to right, Gln24, Gln38, Gln83, Ala126 EPO, a peptide linker having the formula ((Ser-Gly-Gly-Gly-Gly)$_3$-Ser-Pro), and human serum albumin.

In another aspect, the invention features, an EPOa-hSA fusion protein which includes, from left to right, human serum albumin, a peptide linker, e.g., a peptide linker having the formula ((Ser-Gly-Gly-Gly-Gly)$_3$-Ser-Pro), and an EPOa which includes amino acid residues Gln24, Gln38, Gln83 and Ala126.

In a preferred embodiment the EPOa is Gln24, Gln38, Gln83, Ala126 EPO.

In a preferred embodiment the fusion protein is from left to right, human serum albumin, a peptide linker having the formula ((Ser-Gly-Gly-Gly-Gly)$_3$-Ser-Pro), and Gln24, Gln38, Gln83, Ala126 EPO.

In another aspect, the invention features, an isolated nucleic acid having a nucleotide sequence which encodes an EPOa-hSA fusion protein described herein, e.g., an EPOa-hSA fusion protein wherein at least one amino acid residue is altered such that a site which serves as a site for glycosylation in EPO does not serve as a site for glycosylation in the EPOa, e.g., an EPOa-hSA fusion protein in which at least one amino acid residue of the encoded EPOa-hSA which can serve as a glycosylation site in erythropoietin is altered, e.g., by substitution or deletion, such that it does not serve as a glycosylation site.

In another aspect, the invention features, a nucleic acid which encodes an EPOa-hSA fusion protein wherein the EPOa includes amino acid residues Gln24, Gln38, Gln83 and Ala126.

In a preferred embodiment the EPOa is Gln24, Gln38, Gln83, Ala126 EPO.

In another aspect, the invention features, a nucleic acid which encodes an EPOa-hSA fusion protein which includes from left to right, an EPOa which includes amino acid residues Gln24, Gln38, Gln83 and Ala126, a peptide linker, e.g., a peptide linker having the formula ((Ser-Gly-Gly-Gly-Gly)$_3$-Ser-Pro), and human serum albumin.

In a preferred embodiment the EPOa is Gln24, Gln38, Gln83, Ala126 EPO.

In a preferred embodiment the fusion protein is from left to right, Gln24, Gln38, Gln83, Ala126 EPO, a peptide linker having the formula ((Ser-Gly-Gly-Gly-Gly)$_3$-Ser-Pro), and human serum albumin.

In another aspect, the invention features, a nucleic acid which encodes an EPOa-hSA fusion protein which includes, from left to right, human serum albumin, a peptide linker, e.g., a peptide linker having the formula ((Ser-Gly-Gly-Gly-Gly)$_3$-Ser-Pro), and an EPOa which includes amino acid residues Gln24, Gln38, Gln83 and Ala126.

In a preferred embodiment the EPOa is Gln24, Gln38, Gln83, Ala126 EPO.

In a preferred embodiment the fusion protein is from left to right, human serum albumin, a peptide linker having the formula ((Ser-Gly-Gly-Gly-Gly)$_3$-Ser-Pro), and Gln24, Gln38, Gln83, Ala126 EPO.

In another aspect, the invention features, an expression vector or a construct which includes a nucleic acid of the invention.

In a preferred embodiment, the vector or construct further includes: a promoter; a selectable marker; an origin of replication; or a DNA homologous to a species other than human, e.g., goat DNA.

In preferred embodiments, the promoter is a milk specific promoter, e.g., a milk serum protein or casein promoter. The milk specific promoter is a casein promoter, beta lactoglobulin promoter, whey acid protein promoter, or lactalbumin promoter. Preferably, the promoter is a goat β casein promoter.

In another aspect, the invention features, a cell which includes a vector or nucleic acid of the invention.

In another aspect, the invention features, a method of making an EPOa-hSA fusion in a nucleic acid construct or a vector. The method includes, forming in the construct or vector, a sequence in which a nucleic acid which encodes an erythropoietin analog is linked in frame to a nucleic acid which encodes human serum albumin.

In another aspect, the invention features, a method for making an EPOa-hSA fusion protein, e.g., from a cultured cell. The method includes supplying a cell which includes a nucleic acid which encodes an EPOa-hSA fusion protein, and expressing the EPOa-hSA fusion protein from the nucleic acid, thereby making the EPOa-hSA fusion protein.

In a preferred embodiment, the cell is a mammalian, yeast, plant, insect, or bacterial cell. Suitable mammalian cells include CHO cells or other similar expression systems.

In a preferred embodiment, the cell is a microbial cell, a cultured cell, or a cell from a cell line.

In a preferred embodiment, the EPOa-hSA fusion protein is released into culture medium.

In a preferred embodiment, the EPOa-hSA is released into culture medium and the method further includes purifying the EPOa-hSA fusion protein from culture medium.

In a preferred embodiment, the EPOa includes amino acid residues Gln24, Gln38, Gln83 and Ala126.

In a preferred embodiment the EPOa is Gln24, Gln38, Gln83, Ala126 EPO.

In a preferred embodiment, the EPOa-hSA fusion protein includes from left to right, an EPOa which includes amino acid residues Gln24, Gln38, Gln83 and Ala126, a peptide linker, e.g., a peptide linker having the formula ((Ser-Gly-Gly-Gly-Gly)$_3$-Ser-Pro), and human serum albumin.

In a preferred embodiment the fusion protein is from left to right, Gln24, Gln38, Gln83, Ala126 EPO, a peptide linker having the formula ((Ser-Gly-Gly-Gly-Gly)$_3$-Ser-Pro), and human serum albumin.

In a preferred embodiment, the EPOa-hSA fusion protein includes, from left to right, human serum albumin, a peptide linker, e.g., a peptide linker having the formula ((Ser-Gly-Gly-Gly-Gly)$_3$-Ser-Pro), and an EPOa which includes amino acid residues Gln24, Gln38, Gln83 and Ala126.

In a preferred embodiment the fusion protein is from left to right, human serum albumin, a peptide linker having the formula ((Ser-Gly-Gly-Gly-Gly)$_3$-Ser-Pro), and Gln24, Gln38, Gln83, Ala126 EPO.

The invention also includes a cultured cell which includes a nucleic acid which encodes an EPOa-hSA fusion protein, e.g., an EPOa-hSA fusion protein described herein. The invention also includes methods of making such cells, e.g., by introducing into the cell, or forming in the cell, a nucleic acid which encodes an EPOa-hSA fusion protein, e.g., an EPOa-hSA fusion protein described herein.

In another aspect, the invention features, a method of making an EPOa-hSA fusion protein, e.g., an EPOa-hSA described herein. The method includes providing a transgenic organism which includes a transgene which directs the expression of EPOa-hSA fusion protein; allowing the transgene to be expressed; and, preferably, recovering a transgenically produced EPOa-hSA fusion protein, e.g., from the organism or from a product produced by the organism.

In a preferred embodiment, the transgenic organism is a transgenic animal, e.g., a transgenic mammal, e.g., a transgenic dairy animal, e.g., a transgenic goat or a transgenic cow.

In a preferred embodiment, the EPOa-hSA fusion protein is secreted into a bodily fluid and the method further includes purifying the EPOa-hSA fusion protein from the bodily fluid.

In a preferred embodiment, the transgenically produced EPOa-hSA fusion protein is made in a mammary gland of a transgenic mammal, preferably under the control of a milk specific promoter, e.g., a milk serum protein or casein promoter. The milk specific promoter can be a casein promoter, beta lactoglobulin promoter, whey acid protein promoter, or lactalbumin promoter. Preferably, the promoter is a goat β casein promoter.

In preferred embodiments, the EPOa-hSA fusion protein is made in a mammary gland of the transgenic mammal, e.g., a ruminant, e.g., a dairy animal, e.g., a goat or cow.

In preferred embodiments, the EPOa-hSA fusion protein is secreted into the milk of a transgenic mammal at concentrations of at least about 0.2 mg/ml, 0.5 mg/ml, 0.75 mg/ml, 1 mg/ml, 2 mg/ml, 3 mg/ml or higher.

In preferred embodiments the method further includes recovering EPOa-hSA fusion protein from the organism or from a product produced by the organism, e.g., milk, seeds, hair, blood, eggs, or urine.

In yet another embodiment, the EPOa-hSA fusion protein is produced in a transgenic plant.

In a preferred embodiment, the erythropoietin analog includes amino acid residues Gln24, Gln38, Gln83 and Ala126.

In a preferred embodiment the EPOa is Gln24, Gln38, Gln83, Ala126 EPO.

In a preferred embodiment, the EPOa-hSA fusion protein includes from left to right, an EPOa which includes amino acid residues Gln24, Gln38, Gln83 and Ala126, a peptide linker, e.g., a peptide linker having the formula ((Ser-Gly-Gly-Gly-Gly)$_3$-Ser-Pro), and human serum albumin.

In a preferred embodiment the fusion protein is from left to right, Gln24, Gln38, Gln83, Ala126 EPO, a peptide linker having the formula ((Ser-Gly-Gly-Gly-Gly)$_3$-Ser-Pro), and human serum albumin.

In a preferred embodiment, the EPOa-hSA fusion protein includes, from left to right, human serum albumin, a peptide linker, e.g., a peptide linker having the formula ((Ser-Gly-Gly-Gly-Gly)$_3$-Ser-Pro), and an EPOa which includes amino acid residues Gln24, Gln38, Gln83 and Ala126.

In a preferred embodiment the fusion protein is from left to right, human serum albumin, a peptide linker having the formula ((Ser-Gly-Gly-Gly-Gly)$_3$-Ser-Pro), and Gln24, Gln38, Gln83, Ala126 EPO.

In another aspect, the invention features, a method of making a transgenic EPOa-hSA fusion protein, e.g., an EPOa-hSA fusion described herein. The method includes providing a transgenic animal, e.g., goat or a cow, which includes a transgene which provides for the expression of the EPOa-hSA fusion protein; allowing the transgene to be expressed; and, preferably, recovering EPOa-hSA fusion protein, from the milk of the transgenic animal.

In preferred embodiments, the EPOa-hSA fusion protein is made in a mammary gland of the transgenic mammal, e.g., a ruminant, e.g., a goat or a cow.

In preferred embodiments, the EPOa-hSA fusion protein is secreted into the milk of the transgenic mammal, e.g., a ruminant, e.g., a dairy animal, e.g., a goat or a cow.

In preferred embodiments, the EPOa-hSA fusion protein is made under the control of a mammary gland specific promoter, e.g., a milk specific promoter, e.g., a milk serum protein or casein promoter. The milk specific promoter can be a casein promoter, beta lactoglobulin promoter, whey acid protein promoter, or lactalbumin promoter. Preferably, the promoter is a goat β casein promoter.

In preferred embodiments, the EPOa-hSA fusion protein is secreted into the milk of a transgenic mammal at concentrations of at least about 0.2 mg/ml, 0.5 mg/ml, 0.75 mg/ml, 1 mg/ml, 2 mg/ml, 3 mg/ml or higher.

In a preferred embodiment, the EPOa includes amino acid residues Gln24, Gln38, Gln83 and Ala126.

In a preferred embodiment the EPOa is Gln24, Gln38, Gln83, Ala126 EPO.

In a preferred embodiment, the EPOa-hSA fusion protein includes from left to right, an EPOa which includes amino acid residues Gln24, Gln38, Gln83 and Ala126, a peptide linker, e.g., a peptide linker having the formula ((Ser-Gly-Gly-Gly-Gly)$_3$-Ser-Pro), and human serum albumin.

In a preferred embodiment the fusion protein is from left to right, Gln24, Gln38, Gln83, Ala126 EPO, a peptide linker having the formula ((Ser-Gly-Gly-Gly-Gly)$_3$-Ser-Pro), and human serum albumin.

In a preferred embodiment, the EPOa-hSA fusion protein includes, from left to right, human serum albumin, a peptide linker, e.g., a peptide linker having the formula ((Ser-Gly-Gly-Gly-Gly)$_3$-Ser-Pro), and an EPOa which includes amino acid residues Gln24, Gln38, Gln83 and Ala126.

In a preferred embodiment the fusion protein is from left to right, human serum albumin, a peptide linker having the formula ((Ser-Gly-Gly-Gly-Gly)$_3$-Ser-Pro), and Gln24, Gln38, Gln83, Ala126 EPO.

In another aspect, the invention features, a method for providing a transgenic preparation which includes an EPOa-hSA fusion protein, e.g., an EPOa-hSA fusion protein described herein, in the milk of a transgenic mammal. The method includes: providing a transgenic mammal having an EPOa-hSA fusion protein-coding sequence operatively linked to a promoter sequence that results in the expression of the protein-coding sequence in mammary gland epithelial cells, allowing the fusion protein to be expressed, and obtaining milk from the mammal, thereby providing the transgenic preparation.

In a preferred embodiment, the EPOa-hSA fusion protein-coding sequence operatively linked to a promoter sequence is introduced into the germline of the transgenic mammal.

In a preferred embodiment, the erythropoietin analog includes amino acid residues Gln24, Gln38, Gln83 and Ala126.

In a preferred embodiment the EPOa is Gln24, Gln38, Gln83, Alal 26 EPO.

In a preferred embodiment, the EPOa-hSA fusion protein includes from left to right, an EPOa which includes amino acid residues Gln24, Gln38, Gln83 and Ala126, a peptide linker, e.g., a peptide linker having the formula ((Ser-Gly-Gly-Gly-Gly)$_3$-Ser-Pro), and human serum albumin.

In a preferred embodiment the fusion protein is from left to right, Gln24, Gln38, Gln83, Ala126 EPO, a peptide linker having the formula ((Ser-Gly-Gly-Gly-Gly)$_3$-Ser-Pro), and human serun albumin.

In a preferred embodiment, the EPOa-hSA fusion protein includes, from left to right, human serum albumin, a peptide linker, e.g., a peptide linker having the formula ((Ser-Gly-Gly-Gly-Gly)$_3$-Ser-Pro), and an EPOa which includes amino acid residues Gln24, Gln38, Gln83 and Ala126.

In a preferred embodiment the fusion protein is from left to right, human serum albumin, a peptide linker having the formula ((Ser-Gly-Gly-Gly-Gly)$_3$-Ser-Pro), and Gln24, Gln38, Gln83, Ala126 EPO.

In another aspect, the invention features, a method for providing a transgenic preparation which includes an EPOahSA fusion protein, e.g., an EPOa-hSA fusion protein described herein, in the milk of a transgenic goat or transgenic cow. The method includes providing a transgenic goat or cow having an EPOa-hSA fusion protein-coding sequence operatively linked to a promoter sequence that results in the expression of the protein-coding sequence in mammary gland epithelial cells, allowing the fusion protein to be expressed, and obtaining milk from the goat or cow, thereby providing the transgenic preparation.

In a preferred embodiment, the erythropoietin analog includes amino acid residues Gln24, Gln38, Gln83 and Ala126.

In a preferred embodiment the EPOa is Gln24, Gln38, Gln83, Ala126 EPO.

In a preferred embodiment, the EPOa-hSA fusion protein includes from left to right, an EPOa which includes amino acid residues Gln24, Gln38, Gln83 and Ala126, a peptide linker, e.g., a peptide linker having the formula ((Ser-Gly-Gly-Gly-Gly)$_3$-Ser-Pro), and human serum albumin.

In a preferred embodiment the fusion protein is from left to right, Gln24, Gln38, Gln83, Ala126 EPO, a peptide linker having the formula ((Ser-Gly-Gly-Gly-Gly)$_3$-Ser-Pro), and human serum albumin.

In a preferred embodiment, the EPOa-hSA fusion protein includes, from left to right, human serum albumin, a peptide linker, e.g., a peptide linker having the formula ((Ser-Gly-Gly-Gly-Gly)$_3$-Ser-Pro), and an EPOa which includes amino acid residues Gln24, Gln38, Gln83 and Ala126.

In a preferred embodiment the fusion protein is from left to right, human serum albumin, a peptide linker having the formula ((Ser-Gly-Gly-Gly-Gly)$_3$-Ser-Pro), and Gln24, Gln38, Gln83, Ala126 EPO.

In another aspect, the invention features, a transgenic organism, which includes a transgene which encodes an EPOa-hSA fusion protein, e.g., an EPOa-hSA fusion protein described herein.

In a preferred embodiment, the transgenic organism is a transgenic plant or animal. Preferred transgenic animals include: mammals; birds; reptiles; marsupials; and amphibians. Suitable mammals include: ruminants; ungulates; domesticated mammals; and dairy animals. Particularly preferred animals include: mice, goats, sheep, camels, rabbits, cows, pigs, horses, oxen, and llamas. Suitable birds include chickens, geese, and turkeys. Where the transgenic protein is secreted into the milk of a transgenic animal, the animal should be able to produce at least 1, and more preferably at least 10, or 100, liters of milk per year.

In preferred embodiments, the EPOa-hSA fusion protein is under the control of a mammary gland specific promoter, e.g., a milk specific promoter, e.g., a milk serum protein or casein promoter. The milk specific promoter can be a casein promoter, beta lactoglobulin promoter, whey acid protein promoter, or lactalbumin promoter. Preferably, the promoter is a goat β casein promoter.

In a preferred embodiments, the EPOa-hSA fusion protein is secreted into the milk at concentrations of at least about 0.2 mg/ml, 0.5 mg/ml, 0.75 mg/ml, 1 mg/ml, 2 mg/ml, 3 mg/ml or higher.

In a preferred embodiment, the EPOa includes amino acid residues Gln24, Gln38, Gln83 and Ala126.

In a preferred embodiment the EPOa is Gln4, Gln38, Gln83, Ala126 EPO.

In a preferred embodiment, the EPOa-hSA fusion protein includes from left to right, an EPOa which includes amino acid residues Gln24, Gln38, Gln83 and Ala26, a peptide linker, e.g. , a peptide linker having the formula ((Ser-Gly-Gly-Gly-Gly)$_3$-Ser-Pro), and human serum albumin.

In a preferred embodiment the fusion protein is from left to right, Gln124, Gln38, Gln83, Ala126 EPO, a peptide linker having the formula ((Ser-Gly-Gly-Gly-Gly)$_3$-Ser-Pro), and human serum albumin.

In a preferred embodiment, the EPOa-hSA fusion protein includes, from left to right, human serum albumin, a peptide linker, e.g., a peptide linker having the formula ((Ser-Gly-Gly-Gly-Gly)$_3$-Ser-Pro), and an EPOa which includes amino acid residues Gln24, Gln38, Gln83 and Ala126.

In a preferred embodiment the fusion protein is from left to right, human serum albumin, a peptide linker having the formula ((Ser-Gly-Gly-Gly-Gly)$_3$-Ser-Pro), and Gln24, Gln38, Gln83, Ala126 EPO.

In another aspect, the invention features, a transgenic cow, goat or sheep, which includes a transgene which encodes an EPOa-hSA fusion protein, e.g., an EPOa-hSA fusion protein described herein.

In preferred embodiments, the EPOa-hSA fusion protein is under the control of a mammary gland specific promoter, e.g., a milk specific promoter, e.g., a milk serum protein or casein promoter. The milk specific promoter can be a casein promoter, beta lactoglobulin promoter, whey acid protein promoter, or lactalbumin promoter. Preferably, the promoter is a goat β casein promoter.

In preferred embodiments, the EPOa-hSA fusion protein is secreted into the milk at concentrations of at least about 0.2 mg/ml, 0.5 mg/ml, 0.75 mg/ml, 1 mg/ml, 2 mg/ml, 3 mg/ml or higher.

In a preferred embodiment, the EPOa includes amino acid residues Gln24, Gln38, Gln83 and Ala126.

In a preferred embodiment the EPOa is Gln24, Gln38, Gln83, Ala126 EPO.

In a preferred embodiment, the EPOa-hSA fusion protein includes from left to right, an EPOa which includes amino acid residues Gln24, Gln38, Gln83 and Ala126, a peptide linker, e.g., a peptide linker having the formula ((Ser-Gly-Gly-Gly-Gly)$_3$-Ser-Pro), and human serum albumin.

In a preferred embodiment the fusion protein is from left to right, Gln24, Gln38, Gln83, Ala126 EPO, a peptide linker having the formula ((Ser-Gly-Gly-Gly-Gly)$_3$-Ser-Pro), and human serum albumin.

In a preferred embodiment, the EPOa-hSA fusion protein includes, from left to right, human serum albumin, a peptide linker, e.g., a peptide linker having the formula ((Ser-Gly-Gly-Gly-Gly)$_3$-Ser-Pro), and an EPOa which includes amino acid residues Gln24, Gln38, Gln83 and Ala126.

In a preferred embodiment the fusion protein is from left to right, human serum albumin, a peptide linker having the formula ((Ser-Gly-Gly-Gly-Gly)$_3$-Ser-Pro), and Gln24, Gln38, Gln83, Ala126 EPO.

In another aspect, the invention features, a herd of transgenic animals having at least one female and one male transgenic animal, wherein each animal includes an EPOa-hSA fusion protein transgene, e.g., a transgene which encodes an EPOa-hSA fusion protein described herein.

In a preferred embodiment, a transgenic animal of the herd is a mammal, bird, reptile, marsupial or amphibian. Suitable mammals include: ruminants; ungulates; domesticated mammals; and dairy animals. Particularly preferred animals include: mice, goats, sheep, camels, rabbits, cows, pigs, horses, oxen, and llamas. Suitable birds include chickens, geese, and turkeys. Where the transgenic protein is secreted into the milk of a transgenic animal, the animal should be able to produce at least 1, and more preferably at least 10, or 100, liters of milk per year.

In preferred embodiments, the EPOa-hSA fusion protein is under the control of a mammary gland specific promoter, e.g., a milk specific promoter, e.g., a milk serum protein or casein promoter. The milk specific promoter can is a casein promoter, beta lactoglobulin promoter, whey acid protein promoter, or lactalbumin promoter.

In preferred embodiments, the EPOa-hSA fusion protein is secreted into the milk at concentrations of at least about 0.2 mg/ml, 0.5 mg/ml, 0.75 mg/ml, 1 mg/ml, 2 mg/ml, 3 mg/ml or higher.

In a preferred embodiment, the EPOa includes amino acid residues Gln24, Gln38, Gln83 and Ala126.

In a preferred embodiment the EPOa is Gln24, Gln38, Gln83, Ala126 EPO.

In a preferred embodiment, the EPOa-hSA fusion protein includes from left to right, an EPOa which includes amino acid residues Gln24, Gln38, Gln83 and Ala126, a peptide linker, e.g., a peptide linker having the formula ((Ser-Gly-Gly-Gly-Gly)$_3$-Ser-Pro), and human serum albumin.

In a preferred embodiment the fusion protein is from left to right, Gln24, Gln38, Gln83, Ala126 EPO, a peptide linker having the formula ((Ser-Gly-Gly-Gly-Gly)$_3$-Ser-Pro), and human serum albumin.

In a preferred embodiment, the EPOa-hSA fusion protein includes, from left to right, human serum albumin, a peptide linker, e.g., a peptide linker having the formula ((Ser-Gly-Gly-Gly-Gly)$_3$-Ser-Pro), and an EPOa which includes amino acid residues Gln24, Gln38, Gln83 and Ala126.

In a preferred embodiment the fusion protein is from left to right, human serum albumin, a peptide linker having the formula ((Ser-Gly-Gly-Gly-Gly)$_3$-Ser-Pro), and Gln24, Gln38, Gln83, Ala126 EPO.

In another aspect, the invention features, a pharmaceutical composition having a therapeutically effective amount of an EPOa-hSA fusion protein, e.g., an EPOa-hSA fusion protein described herein, and a pharmaceutically acceptable carrier.

In a preferred embodiment, the composition includes milk.

In a preferred embodiment, the EPOa includes amino acid residues Gln24, Gln38, Gln83 and Ala126.

In a preferred embodiment the EPOa is Gln24, Gln38, Gln83, Ala126 EPO.

In a preferred embodiment, the EPOa-hSA fusion protein includes from left to right, an EPOa which includes amino acid residues Gln24, Gln38, Gln83 and Ala126, a peptide linker, e.g., a peptide linker having the formula ((Ser-Gly-Gly-Gly-Gly)$_3$-Ser-Pro), and human serum albumin.

In a preferred embodiment the fusion protein is from left to right, Gln24, Gln38, Gln83, Ala126 EPO, a peptide linker having the formula ((Ser-Gly-Gly-Gly-Gly)$_3$-Ser-Pro), and human serum albumin.

In a preferred embodiment, the EPOa-hSA fusion protein includes, from left to right, human serum albumin, a peptide linker, e.g., a peptide linker having the formula ((Ser-Gly-Gly-Gly-Gly)$_3$-Ser-Pro), and an EPOa which includes amino acid residues Gln24, Gln38, Gln83 and Ala126.

In a preferred embodiment the fusion protein is from left to right, human serum albumin, a peptide linker having the formula ((Ser-Gly-Gly-Gly-Gly)$_3$-Ser-Pro), and Gln24, Gln38, Gln83, Ala126 EPO.

In another aspect, the invention features, a kit having an EPOa-hSA fusion protein, e.g., an EPOa-hSA fusion protein described herein, packaged with instructions for treating a subject in need of eiythropoietin.

In a preferred embodiment, the subject is a patient suffering from anemia associated with renal failure, chronic disease, HIV infection, blood loss or cancer.

In another preferred embodiment, the subject is a preoperative patient.

In a preferred embodiment, the erythropoietin analog includes amino acid residues Gln24, Gln38, Gln83 and Ala126.

In a preferred embodiment the EPOa is Gln24, Gln38, Gln83, Ala126 EPO.

In a preferred embodiment, the EPOa-hSA fusion protein includes from left to right, an EPOa which includes amino acid residues Gln24, Gln38, Gln83 and Ala126, a peptide linker, e.g., a peptide linker having the formula ((Ser-Gly-Gly-Gly-Gly)$_3$-Ser-Pro), and human serum albumin.

In a preferred embodiment the fusion protein is from left to right, Gln24, Gln38, Gln83, Ala126 EPO, a peptide linker having the formula ((Ser-Gly-Gly-Gly-Gly)$_3$-Ser-Pro), and human serum albumin.

In a preferred embodiment, the EPOa-hSA fusion protein includes, from left to right, human serum albumin, a peptide linker, e.g., a peptide linker having the formula ((Ser-Gly-Gly-Gly-Gly)$_3$-Ser-Pro), and an EPOa which includes amino acid residues Gln24, Gln38, Gln83 and Ala126.

In a preferred embodiment the fusion protein is from left to right, human serum albumin, a peptide linker having the formula ((Ser-Gly-Gly-Gly-Gly)$_3$-Ser-Pro), and Gln24, Gln38, Gln83, Ala126 EPO.

In another aspect, the invention features, a purified preparation of an EPOa-hSA fusion protein, e.g., an EPO-hSA fusion protein described herein.

In preferred embodiments, the preparation includes at least 1, 10, 100 or 1000 micrograms of EPOa-hSA fusion protein. In preferred embodiments, the preparation includes at least 1, 10, 100 or 1000 milligrams of EPOa-hSA fusion protein.

In another aspect, the invention features, an EPOa-hSA fusion protein, or a purified preparation thereof, wherein the erythropoietin analog includes amino acid residues Gln24, Gln38, Gln83 and Ala126.

In a preferred embodiment the EPOa is Gln24, Gln38, Gln83, Ala126 EPO.

In preferred embodiments, the preparation includes at least 1, 10, 100 or 1000 micrograms of EPOa-hSA fusion protein. In preferred embodiments, the preparation includes at least 1, 10, 100 or 1000 milligrams of EPOa-hSA fusion protein.

In another aspect, the invention features, an EPOa-hSA fusion protein, or a purified preparation thereof, which includes from left to right, an EPOa which includes amino acid residues Gln24, Gln38, Gln83 and Ala126, a peptide linker, e.g., a peptide linker having the formula ((Ser-Gly-Gly-Gly-Gly)$_3$-Ser-Pro), and human serum albumin.

In a preferred embodiment the EPOa is Gln24, Gln38, Gln83, Ala126 EPO.

In a preferred embodiment the fusion protein is from left to right, Gln24, Gln38, Gln83, Ala126 EPO, a peptide linker having the formula ((Ser-Gly-Gly-Gly-Gly)$_3$-Ser-Pro), and human serum albumin.

In preferred embodiments, the preparation includes at least 1, 10, 100 or 1000 micrograms of EPOa-hSA fusion protein. In preferred embodiments, the preparation includes at least 1, 10, 100 or 1000 milligrams of EPOa-hSA fusion protein.

In another aspect, the invention features, an EPOa-hSA fusion protein, or a purified preparation thereof, which includes, from left to right, human serum albumin, a peptide linker, e.g., a peptide linker having the formula ((Ser-Gly-Gly-Gly-Gly)$_3$-Ser-Pro), and an EPOa which includes amino acid residues Gln24, Gln38, Gln83 and Ala126.

In a preferred embodiment the EPOa is Gln24, Gln38, Gln83, Ala126 EPO.

In a preferred embodiment the fusion protein is from left to right, human serum albumin, a peptide linker having the formula ((Ser-Gly-Gly-Gly-Gly)$_3$-Ser-Pro), and Gln24, Gln38, Gln83, Ala126 EPO.

In preferred embodiments, the preparation includes at least 1, 10, or 100 milligrams of EPOa-hSA fusion protein. In preferred embodiments, the preparation includes at least 1, 10, or 100 grams of EPOa-hSA fusion protein.

In another aspect, the invention features, a method of treating a subject, e.g., a human, in need of erythropoietin. The method includes administering a therapeutically effective amount of an EPOa-hSA fusion protein, e.g., an EPO-hSA fusion protein described herein, to the subject.

In a preferred embodiment, the subject is a patient suffering from anemia associated with renal failure, chronic disease, HIV infection, blood loss or cancer.

In another preferred embodiment, the subject is a preoperative patient.

In preferred embodiments the EPOa-hSA is administered repeatedly, e.g., at least two, three, five, or 10 times.

In a preferred embodiment, the erythropoietin analog includes amino acid residues Gln24, Gln38, Gln83 and Ala126.

In a preferred embodiment the EPOa is Gln24, Gln38, Gln83, Ala126 EPO.

In a preferred embodiment, the EPOa-hSA fusion protein includes from left to right, an EPOa which includes amino acid residues Gln24, Gln38, Gln83 and Ala126, a peptide linker, e.g., a peptide linker having the formula ((Ser-Gly-Gly-Gly-Gly)$_3$-Ser-Pro), and human serum albumin.

In a preferred embodiment the fusion protein is from left to right, Gln24, Gln38, Gln83, Ala126 EPO, a peptide linker having the formula ((Ser-Gly-Gly-Gly-Gly)$_3$-Ser-Pro), and human serum albumin.

In a preferred embodiment, the EPOa-hSA fusion protein includes, from left to right, human serum albumin, a peptide linker, e.g., a peptide linker having the formula ((Ser-Gly-Gly-Gly-Gly)$_3$-Ser-Pro), and an EPOa which includes amino acid residues Gln24, Gln38, Gln83 and Ala126.

In a preferred embodiment the fusion protein is from left to right, human serum albumin, a peptide linker having the formula ((Ser-Gly-Gly-Gly-Gly)$_3$-Ser-Pro), and Gln24, Gln38, Gln83, Ala126 EPO.

In another aspect, the invention features, a method of treating a subject in need of erythropoietin. The method includes delivering or providing a nucleic acid encoding an EPOa-hSA fusion protein, e.g., a fusion protein described herein, to the subject.

In a preferred embodiment, the nucleic acid is delivered to a target cell of the subject.

In a preferred embodiment, the nucleic acid is delivered or provided in a biologically effective carrier, e.g., an expression vector.

In a preferred embodiment, the nucleic acid is delivered or provided in a cell, e.g., an autologous, allogeneic, or xenogeneic cell.

In a preferred embodiment, the EPOa includes amino acid residues Gln24, Gln38, Gln83 and Ala126.

In a preferred embodiment the EPOa is Gln24, Gln38, Gln83, Ala126 EPO.

In a preferred embodiment, the EPOa-hSA fusion protein includes from left to right, an EPOa which includes amino acid residues Gln24, Gln38, Gln83 and Ala126, a peptide linker, e.g., a peptide linker having the formula ((Ser-Gly-Gly-Gly-Gly)$_3$-Ser-Pro), and human serum albumin.

In a preferred embodiment the fusion protein is from left to right, Gln24, Gln38, Gln83, Ala126 EPO, a peptide linker having the formula ((Ser-Gly-Gly-Gly-Gly)$_3$-Ser-Pro), and human serum albumin.

In a preferred embodiment, the EPOa-hSA fusion protein includes, from left to right, human serum albumin, a peptide linker, e.g., a peptide linker having the formula ((Ser-Gly-Gly-Gly-Gly)$_3$-Ser-Pro), and an EPOa which includes amino acid residues Gln24, Gln38, Gln83 and Ala126.

In a preferred embodiment the fusion protein is from left to right, human serum albumin, a peptide linker having the formula ((Ser-Gly-Gly-Gly-Gly)$_3$-Ser-Pro), and Gln24, Gln38, Gln83, Ala126 EPO.

In another aspect, the invention features, a method of making a transgenic organism which has an EPOa-hSA transgene. The method includes providing or forming in a cell of an organism, an EPOa-hSA transgene, e.g., a transgene which encodes an EPOa-hSA fusion protein described herein; and allowing the cell, or a descendent of the cell, to give rise to a transgenic organism.

In a preferred embodiment, the transgenic organism is a transgenic plant or animal. Preferred transgenic animals include: mammals; birds; reptiles; marsupials; and amphibians. Suitable mammals include: ruminants; ungulates; domesticated mammals; and dairy animals. Particularly preferred animals include: mice, goats, sheep, camels, rabbits, cows, pigs, horses, oxen, and llamas. Suitable birds include chickens, geese, and turkeys. Where the transgenic protein is secreted into the milk of a transgenic animal, the animal should be able to produce at least 1, and more preferably at least 10, or 100, liters of milk per year.

In preferred embodiments, the EPOa-hSA fusion protein is under the control of a mammary gland specific promoter, e.g., a milk specific promoter, e.g., a milk serum protein or casein promoter. The milk specific promoter can be a casein promoter, beta lactoglobulin promoter, whey acid protein promoter, or lactalbumin promoter. Preferably, the promoter is a goat β casein promoter.

In preferred embodiments, the organism is a mammal, and the EPOa-hSA fusion protein is secreted into the milk of the transgenic animal at concentrations of at least about 0.2 mg/ml, 0.5 mg/ml, 0.75 mg/ml, 1 mg/ml, 2 mg/ml, 3 mg/ml or higher.

In a preferred embodiment, the EPOa includes amino acid residues Gln24, Gln38, Gln83 and Ala126.

In a preferred embodiment the EPOa is Gln24, Gln38, Gln83, Ala126 EPO.

In a preferred embodiment, the EPOa-hSA fusion protein includes from left to right, an EPOa which includes amino acid residues Gln24, Gln38, Gln83 and Ala126, a peptide linker, e.g., a peptide linker having the formula ((Ser-Gly-Gly-Gly-Gly)$_3$-Ser-Pro), and human serum albumin.

In a preferred embodiment the fusion protein is from left to right, Gln24, Gln38, Gln83, Ala126 EPO, a peptide linker having the formula ((Ser-Gly-Gly-Gly-Gly)$_3$-Ser-Pro), and human serum albumin.

In a preferred embodiment, the EPOa-hSA fusion protein includes, from left to right, human serum albumin, a peptide linker, e.g., a peptide linker having the formula ((Ser-Gly-Gly-Gly-Gly)$_3$-Ser-Pro), and an EPOa which includes amino acid residues Gln24, Gln38, Gln83 and Ala126.

In a preferred embodiment the fusion protein is from left to right, human serum albumin, a peptide linker having the formula ((Ser-Gly-Gly-Gly-Gly)$_3$-Ser-Pro), and Gln24, Gln38, Gln83, Ala126 EPO.

In another aspect, the invention features, an erythropoietin analog (EPOa) protein, or a purified preparation thereof, e.g., the EPOa moiety of an EPOa-hSA fusion protein described herein, wherein at least one amino acid residue is altered such that a site which serves as a site for glycosylation in EPO, does not serve as a site for glycosylation in the EPOa, e.g., an EPOa in which at least one amino acid residue which can serve as a glycosylation site in erythropoietin is altered, e.g., by substitution or deletion, such that it does not serve as a glycosylation site.

In a preferred embodiment, the erythropoietin analog includes amino acid residues Gln24, Gln38, Gln83 and Ala126.

In a preferred embodiment the EPOa is Gln24, Gln38, Gln83, Ala126 EPO.

In another aspect, the invention features, an isolated nucleic acid having a nucleotide sequence which encodes an EPOa described herein.

In another aspect, the invention features, an expression vector or a construct which includes an EPOa nucleic acid described herein.

In a preferred embodiment, the vector or construct further includes: a promoter; a selectable marker; an origin of replication; or a DNA homologous to a species other than human, e.g., goat DNA.

In another aspect, the invention features, a cell which includes a vector or construct which includes an EPOa nucleic acid described herein.

A purified preparation, substantially pure preparation of a polypeptide, or an isolated polypeptide as used herein, means a polypeptide that has been separated from at least one other protein, lipid, or nucleic acid with which it occurs in the cell or organism which expresses it, e.g., from a protein, lipid, or nucleic acid in a transgenic animal or in a fluid, e.g., milk, or other substance, e.g., an egg, produced by a transgenic animal. The polypeptide is preferably separated from substances, e.g., antibodies or gel matrix, e.g., polyacrylamide, which are used to purify it. The polypeptide preferably constitutes at least 10, 20, 50 70, 80 or 95% dry weight of the purified preparation. Preferably, the preparation contains: sufficient polypeptide to allow protein sequencing; at least 1, 10, or 100 µg of the polypeptide; at least 1, 10, or 100 mg of the polypeptide.

As used herein, "human serum albumin" or "hSA" refers to a polypeptide having the amino acid sequence described in Minghetti et al. *J Biol. Chem.* 261:6747–6757, 1986; Lawn et al. *Nucl. Acids Res.* 9:6103, 1981. In preferred embodiments, sequence variations are included wherein one or up to two, five, 10, or 20 amino acid residues have been substituted, inserted or deleted. Variants will have substantially the same immunogenicity, in, e.g., mice, rats, rabbits, primates, baboons, or humans, as does hSA. Variants, when incorporated into a fusion protein which includes EPOa, will result in an EPOa-hSA a fusion which has similar clearance time, in e.g., mice, rabbits, or humans, and activity as does a fusion protein which includes the EPOa and hSA. As used herein, "erythropoietin" or "EPO" refers to a glycoprotein hormone involved in the maturation of erythroid progenitor cells into erythrocytes. The sequence of EPO can be found in Powell, J.S., et al., *Proc. Natl. Acad. Sci. USA*, 83:6465–6469 (1986).

A substantially pure nucleic acid, is a nucleic acid which is one or both of: not immediately contiguous with either one or both of the sequences, e.g., coding sequences, with which it is immediately contiguous (i.e., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a CDNA or a genomic DNA fragment produced by PCR or restriction endonuclease treatment) independent of other DNA sequences. Substantially pure DNA also includes a recombinant DNA which is part of a hybrid gene encoding additional EPOa-hSA fusion protein sequence.

Homology, or sequence identity, as used herein, refers to the sequence similarity between two polypeptide molecules or between two nucleic acid molecules. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology =# of identical positions/total # of positions×100). For example, if 6 of 10, of the positions in two sequences are matched or homologous then the two sequences are 60% homologous or have 60% sequence identity. By way of example, the DNA sequences ATTGCC and TATGGC share 50% homology or sequence identity. Generally, a comparison is made when two sequences are aligned to give maximum homology or sequence identity.

The comparison of sequences and determination of percent homology between two sequences can be accomplished using a mathematical algorithm. A preferred, non-limiting example of a mathematical algorithm utilized for the comparison of sequences is the algorithm of Karlin and Altschul (1990) *Proc. Natl. Acad. Sci. USA* 87:2264–68, modified as in Karlin and Altschul (1993) *Proc. Natl. Acad. Sci. USA* 90:5873–77. Such an algorithm is incorporated into the NBLAST and XBLAST programs (version 2.0) of Altschul, et al. (1990) *J Mol. Biol.* 215:403–10. BLAST nucleotide searches can be performed with the NBLAST program, score=100, wordlength=12 to obtain nucleotide sequences homologous to ITALY nucleic acid molecules of the invention. BLAST protein searches can be performed with the XBLAST program, score=50, wordlength=3 to obtain amino acid sequences homologous to ITALY protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The terms peptides, proteins, and polypeptides are used interchangeably herein.

As used herein, the term transgene means a nucleic acid sequence (encoding, e.g., one or more EPOa-hSA fusion protein polypeptides), which is introduced into the genome of a transgenic organism. A transgene can include one or more transcriptional regulatory sequences and other nucleic acid, such as introns, that may be necessary for optimal expression and secretion of a nucleic acid encoding the fusion protein. A transgene can include an enhancer sequence. An EPOa-hSA fusion protein sequence can be operatively linked to a tissue specific promoter, e.g., mammary gland specific promoter sequence that results in the secretion of the protein in the milk of a transgenic mammal, a urine specific promoter, or an egg specific promoter.

As used herein, the term "transgenic cell" refers to a cell containing a transgene.

A transgenic organism, as used herein, refers to a transgenic animal or plant.

As used herein, a "transgenic animal" is a non-human animal in which one or more, and preferably essentially all, of the cells of the animal contain a transgene introduced by way of human intervention, such as by transgenic techniques known in the art. The transgene can be introduced into the cell, directly or indirectly by introduction into a precursor of the cell, by way of deliberate genetic manipulation, such as by microinjection or by infection with a recombinant virus.

As used herein, a "transgenic plant" is a plant, preferably a multi-celled or higher plant, in which one or more, and preferably essentially all, of the cells of the plant contain a transgene introduced by way of human intervention, such as by transgenic techniques known in the art.

Mammals are defined herein as all animals, excluding humans, that have mammary glands and produce milk.

As used herein, a "dairy animal" refers to a milk producing non-human animal which is larger than a rodent. In preferred embodiments, the dairy animal produce large volumes of milk and have long lactating periods, e.g., cows or goats.

As used herein, the term "plant" refers to either a whole plant, a plant part, a plant cell, or a group of plant cells. The class of plants which can be used in methods of the invention is generally as broad as the class of higher plants amenable to transformation techniques, including both monocotyledonous and dicotyledonous plants. It includes plants of a variety of ploidy levels, including polyploid, diploid and haploid.

As used herein, the term "formulation" refers to a composition in solid, e.g., powder, or liquid form, which includes an EPOa-hSA fusion protein. Formulations can provide therapeutical or nutritional benefits. In preferred embodiments, formulations can include at least one nutritional component other than EPOa-hSA fusion protein. A formulation can contain a preservative to prevent the growth of microorganisms.

As used herein, the term "nutraceutical," refers to a food substance or part of a food, which includes an EPOa-hSA fusion protein. Nutraceuticals can provide medical or health benefits, including the prevention, treatment or cure of a disorder. The transgenic protein will often be present in the nutraceutical at concentration of at least 100 mg/kg, more preferably at least 1 mg/kg, most preferably at least 10 mg/kg. A nutraceutical can include the milk of a transgenic animal.

As used herein, the term "erythropoietin analog" or "EPOa" refers to an EPO molecule which differs from a naturally occurring or recombinant EPO at one or more amino acids. Preferably, the EPO analog differs from a naturally occurring or recombinant human EPO at one or more of the following amino acids: Asn24, Asn38, Asn83 and Ser126. Unless otherwise stated, EPO and EPOa as used herein refer to human EPO and EPOa.

A polypeptide has EPOa-hSA fusion protein biological activity if it has at least one biological activity of EPO or is an antagonist, agonist, or super-agonist of a polypeptide having a biological activity of EPO.

As used herein, the language "subject" includes human and non-human animals. The term "non-human animals" of the invention includes vertebrates, e.g., mammals and non-mammals, such as non-human primates, ruminants, birds, amphibians, reptiles and rodents, e.g., mice and rats. The term also includes rabbits.

Other features and advantages of the invention will be apparent from the following detailed description, and from the claims.

DETAILED DESCRIPTION

The drawings are first described.

Glycosylation

Figure 1:
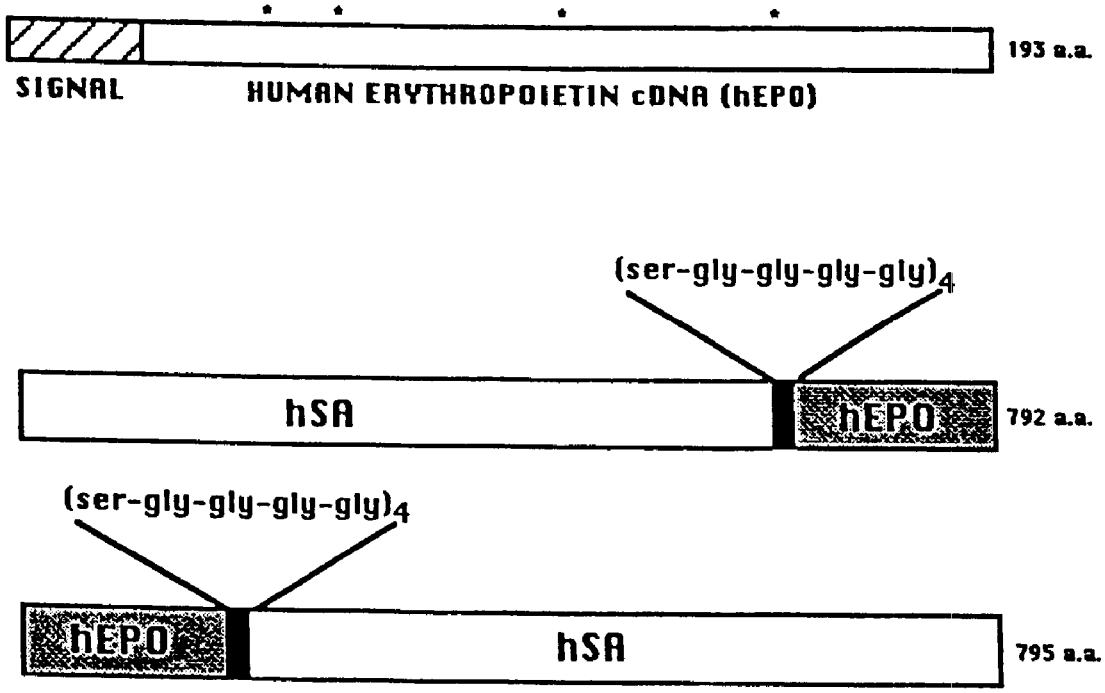
FIG. 1 is a schematic diagram of EPOa-hSA fusion constructs. Asterisks indicate sites of glycosylation of native human erythropoietin.

EPO is a glycoprotein hormone which mediates the maturation of erythroid progenitor cells into erythrocytes. It plays an important role in regulating the level of red blood cells in circulation. Naturally occurring EPO is produced by the liver during fetal life and by the kidney in adults and circulates in the blood and stimulates the production of red blood cells in the bone marrow.

Many cell surface and secretory proteins produced by eucaryotic cells are modified by the attachment of one or more oligosaccharide groups. The modification, referred to as glycosylation, can dramatically affect the physical properties of proteins and can be important in protein stability, secretion, and localization.

Glycosylation occurs at specific locations along the polypeptide backbone. There are usually two major types of glycosylation: glycosylation characterized by O-linked oligosaccharides, which are attached to serine or threonine residues; and glycosylation characterized by N-linked oligosaccharides, which are attached to asparagine residues in an Asn-X-Ser/Thr sequence, where X can be any amino acid except proline. N-acetylneuramic acid (hereafter referred to as sialic acid) is usually the terminal residue of both N-linked and O-linked oligosaccharides.

Human urinary derived EPO contains three N-linked and one O-linked oligosaccharide chains. N-linked glycosylation occurs at asparagine residues located at positions 24, 38 and 83 while O-linked glycosylation occurs at a serine residue located at position 126 (Lai et al. *J. Biol. Chem.* 261, 3116 (1986); Broudy et al, *Arch. Biochem. Biophys.* 265, 329 (1988).

As described herein, EPO analogs of the invention have been modified so that glycosylation at one, two, three, or all of these sites is abolished, e.g., by substitution or deletion of an amino acid residue.

EPO Glycosylation Analogs

An EPO analog can differ from a naturally occurring or recombinant EPO at one or more of the following amino acids: Asn24, Asn38, Asn83 or Ser126. In an EPOa, the primary sequence can be altered such that one or more of these residues fails to support glycosylation.

Preferred analogs are listed below, wherein, Xaa is an amino acid which does not support attachment of a sugar residue, e.g., Gln or Ala

|  | 24 | 38 | 83 | 126 |
| --- | --- | --- | --- | --- |
| wild-type | Asn | Asn | Asn | Ser |
| EPOa-1 | Xaa | Xaa | Xaa | Xaa |
| EPOa-2 | Asn | Xaa | Xaa | Xaa |
| EPOa-3 | Xaa | Asn | Xaa | Xaa |
| EPOa-4 | Xaa | Xaa | Asn | Xaa |
| EPOa-5 | Xaa | Xaa | Xaa | Ser |
| EPOa-6 | Asn | Asn | Xaa | Xaa |
| EPOa-7 | Asn | Xaa | Asn | Ser |
| EPOa-8 | Xaa | Asn | Asn | Xaa |
| EPOa-9 | Xaa | Asn | Asn | Ser |
| EPOa-10 | Xaa | Xaa | Asn | Ser |
| EPOa-11 | Xaa | Asn | Xaa | Ser |
| EPOa-12 | Asn | Xaa | Asn | Xaa |
| EPOa-13 | Asn | Xaa | Asn | Ser |
| EPOa-14 | Asn | Asn | Asn | Xaa |
| EPOa-15 | Asn | Asn | Xaa | Ser |

An EPOa can differ from EPO only at one or more or all of sites 24, 38, 83 and 126 or can have additional amino acid substitutions and/or deletions as discussed below.

EPOa-hSA Fusion Protein Coding Sequences

The preferred EPOa-hSA fusion has one EPOa linked to one hSA molecule but other conformations are within the invention. e.g., EPOa-hSA fusion proteins can have any of the following formula: $R_1$-L-$R_2$; $R_2$-L-$R_1$; $R_1$-L-$R_2$-L-$R_1$; or $R_2$-L-$R_1$-L-$R_2$; $R_1$-$R_{R1}$; $R_1$-$R_2$-$R_1$; or $R_2$-$R_1$-$R_2$; wherein $R_1$ is an EPO analog, $R_2$ is hSA, and L is a peptide linker sequence.

EPOa and hSA domains are linked to each other, preferably via a linker sequence. The linker sequence should separate EPOa and hSA domains by a distance sufficient to ensure that each domain properly folds into its secondary and tertiary structures. Preferred linker sequences (1) should adopt a flexible extended conformation, (2) should not exhibit a propensity for developing an ordered secondary structure which could interact with the functional EPOa and hSA domains, and (3) should have minimal hydrophobic or charged character, which could promote interaction with the functional protein domains. Typical surface amino acids in flexible protein regions include Gly, Asn and Ser. Permutations of amino acid sequences containing Gly, Asn and Ser would be expected to satisfy the above criteria for a linker sequence. Other near neutral amino acids, such as Thr and Ala, can also be used in the linker sequence.

A linker sequence length of 20 amino acids can be used to provide a suitable separation of functional protein domains, although longer or shorter linker sequences may also be used. The length of the linker sequence separating EPOa and hSA can be from 5 to 500 amino acids in length, or more preferably from 5 to 100 amino acids in length. Preferably, the linker sequence is from about 5–30 amino acids in length. In preferred embodiments, the linker sequence is from about 5 to about 20 amino acids, and is advantageously from about 10 to about 20 amino acids. Amino acid sequences useful as linkers of EPOa and hSA include, but are not limited to, $(SerGly_4)_y$, wherein y is greater than or equal to 8, or $Gly_4SerGly_5Ser$. A preferred linker sequence has the formula $(SerGly_4)_4$. Another preferred linker has the sequence $((Ser-Ser-Ser-Ser-Gly)_3$-Ser-Pro).

The EPOa and hSA proteins can be directly fused without a linker sequence. Linker sequences are unnecessary where the proteins being fused have non-essential N-or C-terminal amino acid regions which can be used to separate the functional domains and prevent steric interference. In preferred embodiments, the C-terminus of EPOa can be directly fused to the N-terminus of hSA or the C-terminus of hSA can be directly fused to the N-terminus of EPOa.

Recombinant Production

An EPOa-hSA fusion protein can be prepared with standard recombinant DNA techniques using a nucleic acid molecule encoding the fusion protein. A nucleotide sequence encoding a fusion protein can be synthesized by standard DNA synthesis methods.

A nucleic acid encoding a fusion protein can be introduced into a host cell, e.g., a cell of a primary or immortalized cell line. The recombinant cells can be used to produce the fusion protein. A nucleic acid encoding a fusion protein can be introduced into a host cell, e.g., by homologous recombination. In most cases, a nucleic acid encoding the EPOa-hSA fusion protein is incorporated into a recombinant expression vector.

The nucleotide sequence encoding a fusion protein can be operatively linked to one or more regulatory sequences, selected on the basis of the host cells to be used for expression. The term "operably linked" means that the sequences encoding the fusion protein compound are linked to the regulatory sequence(s) in a manner that allows for expression of the fusion protein. The term "regulatory sequence" refers to promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990), the content of which are incorporated herein by reference. Regulatory sequences include those that direct constitutive expression of a nucleotide sequence in many types of host cells, those that direct expression of the nucleotide sequence only in certain host cells (e.g., tissue-specific regulatory sequences) and those that direct expression in a regulatable manner (e.g., only in the presence of an inducing agent). It will be appreciated by those skilled in the art that the design of the expression vector may depend on such factors as the choice of the host cell to be transformed, the level of expression of fusion protein desired, and the like. The fusion protein expression vectors can be introduced into host cells to thereby produce fusion proteins encoded by nucleic acids.

Recombinant expression vectors can be designed for expression of fusion proteins in prokaryotic or eukaryotic cells. For example, fusion proteins can be expressed in bacterial cells such as *E. coli*, insect cells (e.g., in the baculovirus expression system), yeast cells or mammalian cells. Some suitable host cells are discussed further in Goeddel, *Gene Expression Technology: Methods in Enzy-*

*mology* 185, Academic Press, San Diego, Calif. (1990). Examples of vectors for expression in yeast *S. cerevisiae* include pYepSec1 (Baldari et al., (1987) *EMBO J.* 6:229–234), pMFa (Kurjan and Herskowitz, (1982) Cell 3:933–943), pJRY88 (Schultz et al., (1987) *Gene* 54:113–123), and pYES2 (Invitrogen Corporation, San Diego, Calif.). Baculovirus vectors available for expression of fusion proteins in cultured insect cells (e.g., Sf 9 cells) include the pAc series (Smith et al., (1983) *Mol. Cell. Biol.* 3:2156–2165) and the pVL series (Lucklow, V.A., and Summers, M.D., (1989) *Virology* 170:31–39).

Examples of mammalian expression vectors include pCDM8 (Seed, B., (1987) *Nature* 3:840) and pMT2PC (Kaufman et al. (1987), *EMBO J.* 6:187–195). When used in mammalian cells, the expression vector's control fimctions are often provided by viral regulatory elements. For example, commonly used promoters are derived from polyoma, Adenovirus 2, cytomegalovirus and Simian Virus 40.

In addition to the regulatory control sequences discussed above, the recombinant expression vector can contain additional nucleotide sequences. For example, the recombinant expression vector may encode a selectable marker gene to identify host cells that have incorporated the vector. Moreover, to facilitate secretion of the fusion protein from a host cell, in particular mammalian host cells, the recombinant expression vector can encode a signal sequence operatively linked to sequences encoding the amino-terminus of the fusion protein such that upon expression, the fusion protein is synthesized with the signal sequence fused to its amino terminus. This signal sequence directs the fusion protein into the secretory pathway of the cell and is then cleaved, allowing for release of the mature fusion protein (i.e., the fusion protein without the signal sequence) from the host cell. Use of a signal sequence to facilitate secretion of proteins or peptides from mammalian host cells is known in the art.

Vector DNA can be introduced into prokaryotic or eukaryotic cells via conventional transformation or transfection techniques. As used herein, the terms "transformation" and "transfection" refer to a variety of art-recognized techniques for introducing foreign nucleic acid (e.g., DNA) into a host cell, including calcium phosphate or calcium chloride co-precipitation, DEAE-dextran-mediated transfection, lipofection, electroporation, microinjection and viral-mediated transfection. Suitable methods for transforming or transfecting host cells can be found in Sambrook et al. (*Molecular Cloning: A Laboratory Manual*, 2nd Edition, Cold Spring Harbor Laboratory press (1989)), and other laboratory manuals.

Often only a small fraction of mammalian cells integrate the foreign DNA into their genome. In order to identify and select these integrants, a gene that encodes a selectable marker (e.g., resistance to antibiotics) can be introduced into the host cells along with the gene encoding the fusion protein. Preferred selectable markers include those that confer resistance to drugs, such as G418, hygromycin and methotrexate. Nucleic acid encoding a selectable marker can be introduced into a host cell on the same vector as that encoding the fusion protein or can be introduced on a separate vector. Cells stably transfected with the introduced nucleic acid can be identified by drug selection (e.g., cells that have incorporated the selectable marker gene will survive, while the other cells die).

A recombinant expression vector can be transcribed and translated in vitro, for example using T7 promoter regulatory sequences and T7 polymerase.

Transgenic Mammals

Methods for generating non-human transgenic animals are described herein. DNA constructs can be introduced into the germ line of a mammal to make a transgenic mammal. For example, one or several copies of the construct can be incorporated into the genome of a mammalian embryo by standard transgenic techniques.

It is often desirable to express the transgenic protein in the milk of a transgenic mammal. Mammals that produce large volumes of milk and have long lactating periods are preferred. Preferred mammals are ruminants, e.g., cows, sheep, camels or goats, e.g., goats of Swiss origin, e.g., the Alpine, Saanen and Toggenburg breed goats. Other preferred animals include oxen, rabbits and pigs.

In an exemplary embodiment, a transgenic non-human animal is produced by introducing a transgene into the germline of the non-human animal. Transgenes can be introduced into embryonal target cells at various developmental stages. Different methods are used depending on the stage of development of the embryonal target cell. The specific line(s) of any animal used should, if possible, be selected for general good health, good embryo yields, good pronuclear visibility in the embryo, and good reproductive fitness.

Introduction of the EPOa-hSA fusion protein transgene into the embryo can be accomplished by any of a variety of means known in the art such as microinjection, electroporation, or lipofection. For example, an EPOa-hSA fusion protein transgene can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg can be incubated in vitro for varying amounts of time, or reimplanted into the surrogate host, or both. One common method is to incubate the embryos in vitro for about 1–7 days, depending on the species, and then reimplant them into the surrogate host.

The progeny of the transgenically manipulated embryos can be tested for the presence of the construct by Southern blot analysis of a segment of tissue. An embryo having one or more copies of the exogenous cloned construct stably integrated into the genome can be used to establish a permanent transgenic mammal line carrying the transgenically added construct.

Litters of transgenically altered mammals can be assayed after birth for the incorporation of the construct into the genome of the offspring. This can be done by hybridizing a probe corresponding to the DNA sequence coding for the fusion protein or a segment thereof onto chromosomal material from the progeny. Those mammalian progeny found to contain at least one copy of the construct in their genome are grown to maturity. The female species of these progeny will produce the desired protein in or along with their milk. The transgenic mammals can be bred to produce other transgenic progeny useful in producing the desired proteins in their milk.

Transgenic females may be tested for protein secretion into milk, using an art-known assay technique, e.g., a Western blot or enzymatic assay.

Production of Transgenic Protein in the Milk of a Transgenic Animal

Milk Specific Promoters

Useful transcriptional promoters are those promoters that are preferentially activated in mammary epithelial cells, including promoters that control the genes encoding milk proteins such as caseins, beta lactoglobulin (Clark et al., (1989) *BiolTechnology*7: 487–492), whey acid protein (Gorton et al. (1987) *Bio/Technology* 5: 1183–1187), and lactalbumin (Soulier et al., (1992) *FEBS Letts.* 297: 13). The alpha, beta, gamma or kappa casein gene promoter of any mammalian species can be used to provide mammary expression; a preferred promoter is the goat beta casein gene promoter (DiTullio, (1992) *Bio/Technology*10:74–77). Milk-specific protein promoter or the promoters that are specifically activated in mammary tissue can be isolated from cDNA or genomic sequences. Preferably, they are genomic in origin.

DNA sequence information is available for mammary gland specific genes listed above, in at least one, and often in several organisms. See, e.g., Richards et al., *J. Biol. Chem.* 256, 526–532 (1981) (α-lactalbumin rat); Campbell et al., *Nucleic Acids Res.* 12,8685–8697 (1984) (rat WAP); Jones et al., *J. Biol. Chem.* 260, 7042–7050 (1985) (rat β-casein); Yu-Lee & Rosen, *J. Biol. Chem.* 258, 10794–10804 (1983) (rat γ-casein); Hall, *Biochem. J.* 242, 735–742 (1987) (α-lactalbumin human); Stewart, *Nucleic Acids Res.* 12,389 (1984) (bovine αs1 and κ casein cDNAs); Gorodetsky et al., *Gene* 66,87–96 (1988) (bovine β casein); Alexander et al., *Eur. J. Biochem.* 178, 395–401 (1988) (bovine κ casein); Brignon et al., *FEBS Lett.* 188,48–55 (1977) (bovine αS2 casein); Jamieson et al., *Gene* 61,85–90 (1987), Ivanov et al., *Biol. Chem.* Hoppe-Seyler 369, 425–429 (1988), Alexander et al., *Nucleic Acids Res.* 17, 6739 (1989) (bovine β lactoglobulin); Vilotte et al., *Biochimie* 69, 609–620 (1987) (bovine α-lactalbumin). The structure and function of the various milk protein genes are reviewed by Mercier & Vilotte, J. Dairy Sci. 76, 3079–3098 (1993) (incorporated by reference in its entirety for all purposes). If additional flanking sequence are useful in optimizing expression, such sequences can be cloned using the existing sequences as probes. Mammary-gland specific regulatory sequences from different organisms can be obtained by screening libraries from such organisms using known cognate nucleotide sequences, or antibodies to cognate proteins as probes.

Signal Sequences

Useful signal sequences are milk-specific signal sequences or other signal sequences which result in the secretion of eukaryotic or prokaryotic proteins. Preferably, the signal sequence is selected from milk-specific signal sequences, i.e., it is from a gene which encodes a product secreted into milk. Most preferably, the milk-specific signal sequence is related to the milk-specific promoter used in the expression system of this invention. The size of the signal sequence is not critical for this invention. All that is required is that the sequence be of a sufficient size to effect secretion of the desired recombinant protein, e.g., in the mammary tissue. For example, signal sequences from genes coding for caseins, e.g., alpha, beta, gamma or kappa caseins, beta lactoglobulin, whey acid protein, and lactalbumin are useful in the present invention. A preferred signal sequence is the goat β-casein signal sequence.

Signal sequences from other secreted proteins, e.g., proteins secreted by liver cells, kidney cell, or pancreatic cells can also be used.

DNA Constructs

An EPOa-hSA fusion protein can be expressed from a construct which includes a promoter specific for mammary epithelial cells, e.g., a casein promoter, e.g., a goat beta casein promoter, a milk-specific signal sequence, e.g., a casein signal sequence, e.g., βcasein signal sequence, and a DNA encoding an EPOa-hSA fusion protein.

A construct can also include a 3' untranslated region downstream of the DNA sequence coding for the non-secreted protein. Such regions can stabilize the RNA transcript of the expression system and thus increases the yield of desired protein from the expression system. Among the 3' untranslated regions useful in the constructs of this invention are sequences that provide a poly A signal. Such sequences may be derived, e.g., from the SV40 small t antigen, the casein 3' untranslated region or other 3' untranslated sequences well known in the art. Preferably, the 3' untranslated region is derived from a milk specific protein. The length of the 3' untranslated region is not critical but the stabilizing effect of its poly A transcript appears important in stabilizing the RNA of the expression sequence.

A construct can include a 5' untranslated region between the promoter and the DNA sequence encoding the signal sequence. Such untranslated regions can be from the same control region from which promoter is taken or can be from a different gene, e.g., they may be derived from other synthetic, semi-synthetic or natural sources. Again their specific length is not critical, however, they appear to be useful in improving the level of expression.

A construct can also include about 10%, 20%, 30%, or more of the N-terminal coding region of a gene preferentially expressed in mammary epithelial cells. For example, the N-terminal coding region can correspond to the promoter used, e.g., a goat β-casein N-terminal coding region.

Prior art methods can include making a construct and testing it for the ability to produce a product in cultured cells prior to placing the construct in a transgenic animal. Surprisingly, the inventors have found that such a protocol may not be of predictive value in determining if a normally non-secreted protein can be secreted, e.g., in the milk of a transgenic animal. Therefore, it may be desirable to test constructs directly in transgenic animals, e.g., transgenic mice, as some constructs which fail to be secreted in CHO cells are secreted into the milk of transgenic animals.

Purification from Milk

The transgenic protein can be produced in milk at relatively high concentrations and in large volumes, providing continuous high level output of normally processed peptide that is easily harvested from a renewable resource. There are several different methods known in the art for isolation of proteins from milk.

Milk proteins usually are isolated by a combination of processes. Raw milk first is fractionated to remove fats, for example, by skimming, centrifugation, sedimentation (H. E. Swaisgood, Developments in Dairy Chemistry, I: Chemistry of Milk Protein, Applied Science Publishers, NY, 1982), acid precipitation (U.S. Pat. No. 4,644,056) or enzymatic coagulation with rennin or chymotrypsin (Swaisgood, ibid.). Next, the major milk proteins may be fractionated into either a clear solution or a bulk precipitate from which the specific protein of interest may be readily purified.

U.S. Ser. No. 08/648,235 discloses a method for isolating a soluble milk component, such as a peptide, in its biologically active form from whole milk or a milk fraction by tangential flow filtration. Unlike previous isolation methods, this eliminates the need for a first fractionation of whole milk to remove fat and casein micelles, thereby simplifying the process and avoiding losses of recovery and bioactivity. This method may be used in combination with additional purification steps to further remove contaminants and purify the component of interest.

Production of Transgenic Protein in the Eggs of a Transgenic Animal

An EPOa-hSA fusion protein can be produced in tissues, secretions, or other products, e.g., an egg, of a transgenic animal. EPOa-hSA can be produced in the eggs of a transgenic animal, preferably a transgenic turkey, duck, goose, ostrich, guinea fowl, peacock, partridge, pheasant, pigeon, and more preferably a transgenic chicken, using methods known in the art (Sang et al., Trends Biotechnology, 12:415–20, 1994). Genes encoding proteins specifically expressed in the egg, such as yolk-protein genes and albumin-protein genes, can be modified to direct expression of EPOa-hSA.

Egg Specific Promoters

Useful transcriptional promoters are those promoters that are preferentially activated in the egg, including promoters that control the genes encoding egg proteins, e.g., ovalbumin, lysozyme and avidin. Promoters from the chicken ovalbumin, lysozyme or avidin genes are preferred. Egg-specific protein promoters or the promoters that are specifically activated in egg tissue can be from cDNA or genomic sequences. Preferably, the egg-specific promoters are genomic in origin.

DNA sequences of egg specific genes are known in the art (see, e.g., Burley et al., "The Avian Egg", John Wiley and Sons, p. 472, 1989, the contents of which are incorporated herein by reference). If additional flanking sequence are useful in optimizing expression, such sequences can be cloned using the existing sequences as probes. Egg specific regulatory sequences from different organisms can be obtained by screening libraries from such organisms using known cognate nucleotide sequences, or antibodies to cognate proteins as probes.

Transgenic Plants

An EPOa-hSA fusion protein can be expressed in a transgenic organism, e.g., a transgenic plant, e.g., a transgenic plant in which the DNA transgene is inserted into the nuclear or plastidic genome. Plant transformation is known as the art. See, in general, *Methods in Enzymology* Vol. 153 ("Recombinant DNA Part D") 1987, Wu and Grossman Eds., Academic Press and European Patent Application EP 693554.

Foreign nucleic acid can be introduced into plant cells or protoplasts by several methods. For example, nucleic acid can be mechanically transferred by microinjection directly into plant cells by use of micropipettes. Foreign nucleic acid can also be transferred into a plant cell by using polyethylene glycol which forms a precipitation complex with the genetic material that is taken up by the cell (Paszkowski et al. (1984) *EMBO J.* 3:2712–22). Foreign nucleic acid can be introduced into a plant cell by electroporation (Fromm et al. (1985) *Proc. Natl. Acad. Sci. USA* 82:5824). In this technique, plant protoplasts are electroporated in the presence of plasmids or nucleic acids containing the relevant genetic construct. Electrical impulses of high field strength reversibly permeabilize biomembranes allowing the introduction of the plasmids. Electroporated plant protoplasts reform the cell wall, divide, and form a plant callus. Selection of the transformed plant cells with the transformed gene can be accomplished using phenotypic markers.

Cauliflower mosaic virus (CaMV) can be used as a vector for introducing foreign nucleic acid into plant cells (Hohn et al. (1982) "Molecular Biology of Plant Tumors," Academic Press, New York, pp. 549–560; Howell, U.S. Pat. No. 4,407,956). CaMV viral DNA genome is inserted into a parent bacterial plasmid creating a recombinant DNA molecule which can be propagated in bacteria. The recombinant plasmid can be further modified by introduction of the desired DNA sequence. The modified viral portion of the recombinant plasmid is then excised from the parent bacterial plasmid, and used to inoculate the plant cells or plants.

High velocity ballistic penetration by small particles can be used to introduce foreign nucleic acid into plant cells. Nucleic acid is disposed within the matrix of small beads or particles, or on the surface (Klein et al. (1987) *Nature* 327:70–73). Although typically only a single introduction of a new nucleic acid segment is required, this method also provides for multiple introductions.

A nucleic acid can be introduced into a plant cell by infection of a plant cell, an explant, a meristem or a seed with *Agrobacterium tumefaciens* transformed with the nucleic acid. Under appropriate conditions, the transformed plant cells are grown to form shoots, roots, and develop further into plants. The nucleic acids can be introduced into plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al. (1984) "Inheritance of Functional Foreign Genes in Plants," *Science* 233:496–498; Fraley et al. (1983) *Proc. Natl. Acad. Sci. USA* 80:4803).

Plants from which protoplasts can be isolated and cultured to give whole regenerated plants can be transformed so that whole plants are recovered which contain the transferred foreign gene. Some suitable plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, and Datura.

Plant regeneration from cultured protoplasts is described in Evans et al., "Protoplasts Isolation and Culture," *Handbook of Plant Cell Cultures* 1:124–176 (MacMillan Publishing Co. New York 1983); M. R. Davey, "Recent Developments in the Culture and Regeneration of Plant Protoplasts," Protoplasts (1 983)-Lecture Proceedings, pp. 12–29, (Birkhauser, Basal 1983); P.J. Dale, "Protoplast Culture and Plant Regeneration of Cereals and Other Recalcitrant Crops," Protoplasts (1983)-Lecture Proceedings, pp. 31–41, (Birkhauser, Basel 1983); and H. Binding, "Regeneration of Plants," Plant Protoplasts, pp. 21–73, (CRC Press, Boca Raton 1985).

Regeneration from protoplasts varies from species to species of plants, but generally a suspension of transformed protoplasts containing copies of the exogenous sequence is first generated. In certain species, embryo formation can then be induced from the protoplast suspension, to the stage of ripening and germination as natural embryos. The culture media can contain various amino acids and hormones, such as auxin and cytokinins. It can also be advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In vegetatively propagated crops, the mature transgenic plants can be propagated by the taking of cuttings or by tissue culture techniques to produce multiple identical plants for trialling, such as testing for production characteristics. Selection of a desirable transgenic plant is made and new varieties are obtained thereby, and propagated vegetatively for commercial sale. In seed propagated crops, the mature transgenic plants can be self crossed to produce a homozygous inbred plant. The inbred plant produces seed containing the gene for the newly introduced foreign gene activity level. These seeds can be grown to produce plants that have the selected phenotype. The inbreds according to this invention can be used to develop new hybrids. In this method a selected inbred line is crossed with another inbred line to produce the hybrid.

Parts obtained from a transgenic plant, such as flowers, seeds, leaves, branches, fruit, and the like are covered by the invention, provided that these parts include cells which have been so transformed. Progeny and variants, and mutants of the regenerated plants are also included within the scope of this invention, provided that these parts comprise the introduced DNA sequences. Progeny and variants, and mutants of the regenerated plants are also included within the scope of this invention.

Selection of transgenic plants or plant cells can be based upon a visual assay, such as observing color changes (e.g., a white flower, variable pigrnent production, and uniform color pattern on flowers or irregular patterns), but can also involve biochemical assays of either enzyme activity or product quantitation. Transgenic plants or plant cells are grown into plants bearing the plant part of interest and the gene activities are monitored, such as by visual appearance (for flavonoid genes) or biochemical assays (Northern blots); Western blots; enzyme assays and flavonoid compound assays, including spectroscopy, see, Harborne et al. (Eds.), (1975) The Flavonoids, Vols. 1 and 2, [Acad. Press]). Appropriate plants are selected and further evaluated. Methods for generation of genetically engineered plants are further described in U.S. Pat. No. 5,283,184, U.S. Pat. No. 5,482,852, and European Patent Application EP 693 554, all of which are hereby incorporated by reference.

Other Erythropoietin Analogs

Preferably, EPO analogs have one or more changes in the following amino acids: Asn24, Asn38, Asn83 or Ser126. EPO analogs can also have additional amino acid changes, as is discussed below.

In a preferred embodiment, the EPOa differs in amino acid sequence at up to 1, 2, 3, 5, or 10 residues, from the sequence of naturally occurring EPO protein. These changes can be in addition to changes at Asn24, Asn38, Asn83, and Ser126. In other preferred embodiments, the EPOa differs in amino acid sequence at up to 1, 2, 3, 5, or 10 % of the residues from a sequence of naturally occurring EPO protein. These changes can be in addition to changes at Asn24, Asn38, Asn 83, and Ser126. In preferred embodiments, the differences are such that the erythropoietin analog exhibits an erythropoietin biological activity when fused to hSA. In preferred embodiments, one or more, or all of the differences are conservative amino acid changes. In other preferred embodiments, one or more, or all of the differences are other than conservative amino acid changes.

In preferred embodiments, the EPOa is a fragment, e.g., a terminal fragment on a sequence from which an interval subsequence has been deleted, of a full length erythropoietin.

In preferred embodiments: the fragment is at least 50, 60, 80, 100 or 150 amino acids in length; the fragment has a biological activity of a naturally occurring erythropoietin; the fragment is either, an agonist or an antagonist, of a biological activity of a naturally occurring erythropoietin; the fragment can inhibit, e.g., competitively or non competitively inhibit, the binding of erythropoietin to a receptor.

In preferred embodiments, the fragment it has at least 60, and more preferably at least 70, 80, 90, 95, 99, or 100 % sequence identity with the corresponding amino acid sequence of naturally occurring erythropoietin.

In preferred embodiments, the fragment is a fragment of a vertebrate, e.g., a mammalian, e.g. a primate, e.g., a human erythropoietin.

In a preferred embodiment, the fragment differs in amino acid sequence at up to 1, 2, 3, 5, or 10 residues, from the corresponding residues of naturally occurring erythropoietin. These changes can be in addition to changes at Asn24, Asn38, Asn83, and Ser126. In other preferred embodiments, the fragment differs in amino acid sequence at up to 1, 2, 3, 5, or 10% of the residues from the corresponding residues of naturally occurring erythropoietin. These changes can be in addition to changes at Asn24, Asn38, Asn83, and Ser126. In preferred embodiments, the differences are such that the fragment exhibits an erythropoietin biological activity when fused to hSA. In preferred embodiments, one or more, or all of the differences are conservative amino acid changes. In other preferred embodiments one or more, or all of the differences are other than conservative amino acid changes.

Polypeptides of the invention include those which arise as a result of alternative translational and postranslational events.

Numerous analogs of EPO are known in the art. The primary structure and activity of these variants can serve as guidance for the introduction of additional changes (in addition to changes which modify glycosylation) into an EPOa. Changes which reduce activity, or create glycosylation sites, should be avoided.

Some of the EPO analogs known in the art are outlined in Table 1 below.

TABLE 1

| EPO mutation | Loc. | Type | Effect | Source | Reference |
|---|---|---|---|---|---|
| Pro-Asn | 2 | Substitution | No increase in biological activity | hEPO | U.S. Pat. No. 4703008 Kiren-Amgen, Inc. |
|  | 2–6 | Deletion | No increase in biological activity | hEPO | U.S. Pat. No. 4703008 Kiren-Amgen, Inc. |
| Cys-His | 7 | Substitution | Eliminates biological activity | hEPO | U.S. Pat. No. 4703008 Kiren-Amgen, Inc. |
| Tyr-Phe | 15 | Substitution | No increase in biological activity | hEPO | U.S. Pat. No. 4703008 Kiren-Amgen, Inc. |
|  | 15 | Substitution or Deletion | Retains in-vivo activity in animals but there is no increase in EPO |  | WO 9425055 Abbott Labs. |

TABLE 1-continued

| EPO mutation | Loc. | Type | Effect | Source | Reference |
|---|---|---|---|---|---|
| Asn-? | 24 | Substitution | Reduces biological activity | hEPO | WO 9425055 Abbott Labs. |
|  | 24 | Substitution or Deletion | Retains in-vivo activity in animals but there is no increase in EPO precursors |  | WO 9425055 Abbott Labs. |
|  | 27–55 | Deletion | No increase in biological activity | hEPO | U.S. Pat. No. 4703008 Kiren-Amgen, Inc. |
| Cys-Pro | 33 | Substitution | Loss of in-vitro activity. The disulfide bond between Cys29-Cys33 is essential for function | hEPO | WO 9425055 Abbott Labs. |
| Asn-? | 38 | Substitution | Intracellular degradation and lack of secretion | hEPO | WO 9425055 Abbott Labs. |
| Tyr-Phe | 49 | Substitution | No increase in biological activity | hEPO | U.S. Pat. No. 4703008 Kiren-Amgen, Inc. |
|  | 49 | Substitution or Deletion | Retains in-vivo activity in animals but there is no increase in EPO precursors |  | WO 9425055 Abbott Labs. |
| Met-? | 54 | Substitution | Retains in-vivo activity and is less susceptible to oxidation | hEPO | U.S. Pat. No. 4835260 Genetics Institute, Inc |
| Met-Leu | 54 | Substitution | Retains biological activity | hEPO | U.S. Pat. No. 4835260 Genetics Institute, Inc |
| Leu-Asn | 69 | Substitution | Creates an additional N-glycosylation site |  | EP 0428267B1 AMGEN |
|  | 76 | Substitution or Deletion | Retains in-vivo activity in animals but there is no increase in EPO precursors |  | U.S. Pat. No. 4703008 Kiren-Amgen, Inc. |
|  | 78 | Substitution or Deletion | Retains in-vivo activity in animals but there is no increase in EPO precursors |  | U.S. Pat. No. 4703008 Kiren-Amgen, Inc. |
|  | 83 | Substitution or Deletion | Retains in-vivo activity in animals but there is no increase in EPO precursors |  | U.S. Pat. No. 4703008 Kiren-Amgen, Inc. |
| Domain1 | 99–119 | Deletion | Rapidly degraded and inactive in-vitro |  | WO 9425055 Abbott Labs. |
| Domain2 | 111–129 | Deletion | Retain in-vitro activity |  |  |
| Ala-Pro | 124 | Double Substitution | Creates additional N- and O- glycosylation sites |  | EP 0428267B1 AMGEN |
| Ala-Thr | 125 | Substitution | Creates additional O-glycosylation site |  | EP 0428267B1 AMGEN |
| Ala-Asn | 125 | Double Substitution | Creates an additional N-glycosylation site |  | EP 0428267B1 AMGEN |
| Ala-Ser | 127 |  | Creates an additional O-glycosylation site |  |  |
| Ser-? | 126 | Substitution | Rapid degradation or lack of secretion |  | U.S. Pat. No. 4703008 Kiren-Amgen, Inc. |
| Cys-Pro Then Arg-Cys | 33 139 | Double Substitution | Loss of activity Restores and improves in-vivo activity |  | WO 9425055 Abbott Labs. |
|  | 143 | Substitution or Deletion | Retains in-vivo activity in animals but there is no increase in EPO precursors |  | U.S. Pat. No. 4703008 Kiren-Amgen, Inc. |
| Tyr-Phe | 145 | Substitution | No increase in biological activity |  | U.S. Pat. No. 4703008 Kiren-Amgen, Inc. |
|  | 145 | Substitution or Deletion | Retains in-vivo activity in animals but there is no increase in EPO precursors |  | U.S. Pat. No. 4703008 Kiren-Amgen, Inc. |
|  | 160 | Substitution or Deletion | Retains in-vivo activity in animals but there is no increase in EPO |  | U.S. Pat. No. 4703008 Kiren-Amgen, Inc. |

TABLE 1-continued

| EPO mutation | Loc. | Type | Effect | Source | Reference |
|---|---|---|---|---|---|
| | 161 | Substitution or Deletion | Retains in-vivo activity in animals but there is no increase in EPO precursors | | U.S. Pat. No. 4703008 Kiren-Amgen, Inc. |
| | 162 | Substitution or Deletion | Retains in-vivo activity in animals but there is no increase in EPO precursors | | U.S. Pat. No. 4703008 Kiren-Amgen, Inc. |
| | 163 | Substitution or Deletion | Retains in-vivo activity in animals but there is no increase in EPO precursors | | U.S. Pat. No. 4703008 Kiren-Amgen, Inc. |
| | 164 | Substitution or Deletion | Retains in-vivo activity in animals but there is no increase in EPO precursors | | U.S. Pat. No. 4703008 Kiren-Amgen, Inc. |
| | 165 | Substitution or Deletion | Retains in-vivo activity in animals but there is no increase in EPO precursors | | U.S. Pat. No. 4703008 Kiren-Amgen, Inc. |
| | 166 | Substitution or Deletion | Retains in-vivo activity in animals but there is no increase in EPO precursors | | U.S. Pat. No. 4703008 Kiren-Amgen, Inc. |
| | 163–166 | Deletion | No increase in biological activity | | U.S. Pat. No. 4703008 Kiren-Amgen, Inc. |
| Ser-? | 183 | Substitution | Intracellular degradation and lack of secretion | | U.S. Pat. No. 4703008 Kiren-Amgen, Inc. |

Although hSA is the preferred fusion partner other polypeptides can be used. Preferably these are polypeptides which do not support glycosylation. The phrase "do not support glycosylation" as used herein refers to polypeptides which naturally do not support glycosylation and polypeptides which have been modified such that it does not support glycosylation. For example, the fusion partner can be a soluble fragment of Ig, preferably a soluble fragment of Ig modified such that it does not support glycosylation.

In any embodiment described herein, the hSA moiety of a fusion can be replaced with another protein, preferably a protein, e.g., a plasma protein or fragment thereof, which can improve the circulating half life of EPO or an EPOa. For example, the fusion protein can be an EPOa-immunoglobulin (Ig) fusion protein in which the EPOa sequence is fused to a sequence derived from the immunoglobulin superfamily. Several soluble fusion protein constructs have been disclosed wherein the extracellular domain of a cell surface glycoprotein is fused with the constant F(c) region of an immunoglobulin. For example, Capon et al. (1989) *Nature* 337(9):525–531, provide guidance on generating a longer lasting CD4 analog by fusing CD4 to an immunoglobulin (IgG1). See also, Capon et al., U.S. Pat. Nos. : 5,116,964 and 5,428,130 (CD4-IgG fusion constructs); Linsley et al., U.S, Pat. No. 5,434,131 (CTLA4-IgG1 and B7-IgG1 fusion constructs); Linsley et al. (1991) *J. Exp. Med.* 174:561–569 (CTLA4-IgG1 fusion constructs); and Linsley et al. (1991) *J. Exp. Med* 173:721–730 (CD28-IgG1 and B7-IgG1 fusion constructs). Such fusion proteins have proven useful for modulating receptor-ligand interactions and reducing inflammation in vivo. For example, fusion proteins in which an extracellular domain of cell surface tumor necrosis factor receptor (TNFR) proteins has been fused to an immunoglobulin constant (Fc) region have been used in vivo. See, for example, Moreland et al. (1997) *N. Engl. J. Med.* 337(3):141–147; and, van der Poll et al. (1997) *Blood* 89(10):3727–3734).

Pharmaceutical Compositions

An EPOa-hSA fusion protein or nucleic acid can be incorporated into a pharmaceutical composition useful to treat, e.g., inhibit, attenuate, prevent, or ameliorate, a condition characterized by an insufficient level of EPO activity, including conditions where the level of EPO activity is normal (but still insufficient) and those in which it is less from normal.

Preferably, the preparation of invention will be administered to a subject suffering from renal failure, chronic disease, HIV infection, blood loss or cancer, or a pre-operative patient. The compositions should contain a therapeutic or prophylactic amount of the recombinantly produced EPOa-hSA fusion protein, in a pharmaceutically-acceptable carrier or in the milk of the transgenic animal.

The pharmaceutical carrier can be any compatible, non-toxic substance suitable to deliver the polypeptides to the patient. Sterile water, alcohol, fats, waxes, and inert solids may be used as the carrier. Pharmaceutically-acceptable adjucants, buffering agents, dispersing agents, and the like, may also be incorporated into the pharmaceutical compositions. The carrier can be combined with the EPO-hSA fusion protein in any form suitable for administration by injection (usually intravenously or subcutaneously) or otherwise. For intravenous administration, suitable carriers include, for example, physiological saline, bacteriostatic water, Cremophor EL™ (BASF, Parsippany, N.J.) or phosphate buffered saline (PBS). The concentration of the transgenically produced peptide or other active agent in the pharmaceutical composition can vary widely, i.e., from less than about 0.1% by weight, usually being at least about 1% weight to as much as 20% by weight or more.

For intravenous administration of the EPO-hSA fusion protein, the composition must be sterile and should be fluid to the extent that easy syringability exists. It must be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

For nasal administration, the polypeptides can be formulated as aerosols. The term "aerosol" includes any gas-borne suspended phase of the compounds of the instant invention which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of a compound of the instant invention suspended in air or other carrier gas, which may be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273–313; and Raeburn et al. (1992) *J. Pharmacol. Toxicol. Methods* 27:143–159.

Dosage of the EPO-hSA fusion proteins of the invention may vary somewhat from individual to individual, depending on the particular peptide and its specific in vivo activity, the route of administration, the medical condition, age, weight or sex of the patient, the patient's sensitivities to the EPO-hSA fusion protein or components of vehicle, and other factors which the attending physician will be capable of readily taking into account.

EPOa-hSA can be provided in a sterile container which includes dialysis solution or in a sterile container, e.g., a bag, with saline, blood, plasma, a blood substitute, or other component to be delivered to a patient.

Nutraceuticals

An EPOa-hSA fusion protein can be included in a nutraceutical. Preferably, it includes milk or milk product obtained from a transgenic mammal which expresses fusion protein. It can include plant or plant product obtained from a transgenic plant which expresses the fusion protein. The fusion protein can be provided in powder or tablet form, with or without other known additives, carriers, fillers and diluents. Nutraceuticals are described in Scott Hegenhart, Food Product Design, Dec. 1993. The nutraceutical can be an infant feeding formula. It can include components of a transgenic plant which produces an EPOa-hSA fusion protein.

Gene Therapy

EPOa-hSA constructs can be used as a part of a gene therapy protocol to deliver nucleic acids encoding an EPOa-hSA fusion protein.

A preferred approach for in vivo introduction of nucleic acid into a cell is by use of a viral vector containing nucleic acid, encoding a EPO-hSA fusion protein. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous nucleic acid molecules encoding EPO-hSA fusion protein in vivo. These vectors provide efficient delivery of nucleic acids into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A.D. (1990) *Blood* 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals.

Another viral gene delivery system useful in the present invention uses adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267).

Another viral vector system useful for delivery of the subject nucleotide sequence encoding EPO-hSA fusion protein is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. BioL.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol* 2:32–39; Tratschin et al. (1984) *J. Virol.* 51:611–619; and Flotte et al. (1993) *J. Biol. Chem.* 268:3781–3790).

In addition to viral transfer methods, such as those illustrated above, non-viral methods can also be employed to cause expression of a EPO-hSA fusion protein in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject nucleotide molecule by the targeted cell. Exemplary gene delivery systems of this type include liposomal derived systems, polylysine conjugates, and artificial viral envelopes.

In a representative embodiment, a nucleic acid molecule encoding EPO-hSA fusion protein can be entrapped in liposomes bearing positive charges on their surface (e.g., lipofectins) and (optionally) which are tagged with antibodies against cell surface antigens of the target tissue (Mizuno et al. (1992) No Shinkei Geka 20:547–551; PCT publication WO91/06309; Japanese patent application 1047381; and European patent publication EP-A-25 43075).

Gene delivery systems for the a gene encoding a EPO-hSA fusion protein can be introduced into a patient by any of a number of methods. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. 5,328,470) or by Stereotactic injection (e.g. Chen et al. (1994) *PNAS* 91: 3054–3057).

The pharmaceutical preparation of the gene therapy construct can consist essentially of the gene delivery system in an acceptable diluent, or can comprise a slow release matrix in which the gene delivery vehicle is imbedded. Where the fusion protein can be produced intact from recombinant cells, e.g. retroviral vectors, the pharmaceutical preparation can comprise one or more cells which produce the fusion protein.

OTHER EMBODIMENTS

Other Transgenic Animals

EPOa-hSA fusion protein can be expressed from a variety of transgenic animals. A protocol for the production of a transgenic pig can be found in White and Yannoutsos, *Current Topics in Complement Research*: 64th Forum in Immunology, pp. 88–94; U.S. Pat. No. 5,523,226; U.S. Pat. No. 5,573,933; PCT Application WO 93/25071; and PCT Application WO 95/04744. A protocol for the production of a transgenic mouse can be found in U.S. Pat. No. 5,530,177. A protocol for the production of a transgenic rat can be found in Bader and Ganten, *Clinical and Experimental Pharmacology and Physiology*, Supp. 3: S81–S87, 1996. A protocol for the production of a transgenic cow can be found in *Transgenic Animal Technology, A Handbook*, 1994, ed., Carl A. Pinkert, Academic Press, Inc. A protocol for the production of a transgenic sheep can be found in *Transgenic Animal Technology, A Handbook*, 1994, ed., Carl A. Pinkert, Academic Press, Inc. A protocol for the production of a transgenic rabbit can be found in Hammer et al., *Nature* 315:680–683, 1985 and Taylor and Fan, *Frontiers in Bioscience* 2:d298–308, 1997.

Embodiments of the invention are further illustrated by the following examples which should not be construed as being limiting. The contents of all cited references (including literature references, issued patents, published patent applications, and co-pending patent applications) cited throughout this application are hereby expressly incorporated by reference.

EXAMPLES

Example 1

EPOa-hSA Fusion Constructs

The cDNA encoding the human erythropoietin analog used in the EPOa-hSA fusions was designed and engineered to alter the three N-linked and one O-linked sites of glycosylation (residues 24, 38, 83, and 126, respectively). Furthermore, without altering the remaining amino acid residues, codon usage was changed using a mammary gland protein codon usage table to maximize protein expression in the milk of transgenic animals. A schematic representation of the fusion constructs is outlined in FIG. 1. In the case where hSA is the N-terminal half of the fusion protein, the hSA signal peptide was left intact and the human erythropoietin analog signal was deleted. When the human erythropoietin analog is the N-terminal part of the fusion, its signal sequence was left intact and that of the hSA protein was deleted. Also, in the first case, the wildtype hSA stop codon has been removed as was that of the human erythropoietin analog cDNA in the second construct. In addition, a linker protein (Ser-Gly$_4$)$_4$, or hinge, was placed between the two fusion partners to minimize any inhibitory constraint that hSA might have on the EPO portion of the molecule and its subsequent activity.

The cDNA fusion constructs were put into the appropriate vectors for expression in tissue culture and in the mammary gland of transgenic mice. By expressing these constructs transiently in tissue culture (COS7 cells), a number of important features of the products of these cDNA fusions can be examined, e.g., (1) are the proteins being made and secreted? (2) Are these proteins authentic, recognizable by antisera against EPOa and hSA? (3) Are these proteins bioactive in vitro and in vivo?

Example 2
COS7 Cell Transfections/Western Blot Analysis

Figure 2:
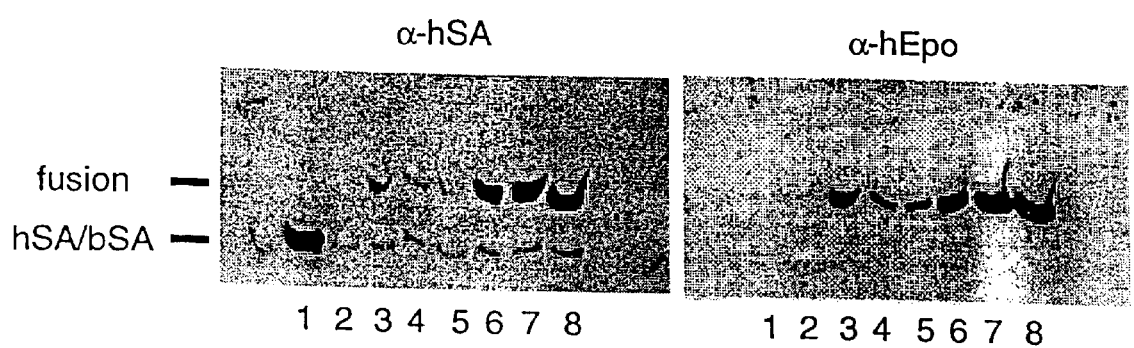
FIG. 2 is a photograph depicting the Western blot analysis of COS7 cells transiently transfected with EPOa-hSA cDNA constructs.

COS7 cells were transiently transfected with fusion cDNA constructs in triplicate plates or a single plate with the vector (pcDNA3) alone. Twenty-four hours after transfection, the media were replaced with a reduced serum medium (Optimem). After five days, all media were harvested and contaminating cells were removed by centrifugation. Samples of the conditioned media were then analyzed by SDS-PAGE and immunuoblotting (see FIG. 2).

Supernatants from COS cells transfected with HIP/pcDNA3 constructs or pcDA3 alone (mock) were analyzed by immunoblotting with a polyclonal antibody against human serum albumin (α-hSA). After analysis with the hSA antibody, the blot was stripped and reanalyzed with a monoclonal antibody against human erythropoietin (α-hEpo). The gel was loaded as follows: lane 1, 10 ng hSA standard; lane 2, 10 $\mu$l mock CM; lanes 3–5, 10 $\mu$l hSA-hEpo CM; lanes 6–8, 10 $\mu$l hEpo-hSA CM.

The results of the Western blotting experiments clearly indicate that a soluble, secreted protein was produced. Both fusion proteins are the appropriate predicted size (~89kDa). The band seen in the conditioned media lanes in the hSA antibody blot represents not hSA ($\mu$66kDa) but bSA, as this antibody has some cross reactivity with the bSA found in the tissue culture medium used. Most importantly, however, is the ability of the two antibodies to recognize both fusion proteins. This suggests that proper translation of the entire fusion construct mRNAs has been accomplished, leaving the appropriate epitopes intact and accessible to the antibodies.

Example 3
Bioactivity

An ELISA was performed with the same α-hSA antibody used in the above Western blot analysis to determine the concentrations of the two fusion proteins in the tissue culture supernatant. Consistent with the Western blot results, the EPOa-linker-hSA fusion protein was shown to be made at approximately 4-fold higher levels than the hSA-linker-EPOa fusion protein (232ng/ml versus 59 ng/ml, respectively). These levels should provide sufficient product to assess in vitro and, possibly, in vivo bioactivity. If the EPOa fraction of the fusion proteins is 20% of the total size of the molecule, 232 ng/ml represents approximately 10 U/ml hEpo-hSA fusion protein [$(2.1 \times 10^5$ U/mg)$2.32 \times 10^{-4}$ mg/ml) (0.2)=9.7 U/ml]. In vitro EPOa activity will be assessed using Epo-responsive cell lines. Briefly, cells are incubated 22–72 hours with increasing amounts of recombinant EPOa-hSA fusion protein and cellular growth is determined by [$^3$H] thymidine uptake or by the colorimetric MTT assay (Sigma).

EPOa-hSA fusion protein can be rapidly purified to near homogeneity using cation exchange chromatography which takes advantage of well characterized hSA binding properties. Fusion proteins can be concentrated if necessary and tested in mice. Mice can be subcutaneously injected with fusion protein (possibly with as little as 3×50 ng/mouse, total EPOa) and responsiveness detected by determining changes in reticulocyte numbers or Hematocrit levels. Direct intramuscular injection, at high concentration (>100 $\mu$g), of the pcDNA3-based plasmid DNA and subsequent monitoring of changes in reticulocyte and Hematocrit levels can be used as an in vivo assay. Plasmid injection has been demonstrated to significantly raise Hematocrit levels in mice when using the wildtype hEpo cDNA expressed from the cytomegalovirus promoter (CMV).

Example 4
Generation of a Erythropoietin Analog-human Serum Albumin (EPOa-hSA) Fusion Protein Construct cDNA encoding EPOa-hSA fusion protein was introduced in the BC355 vector containing the regulatory elements of the goat beta-casein gene, creating a transgene having the EPOa-hSA fusion protein sequence under the control of a milk specific promoter. This construct was used to target EPOa-hSA fusion protein expression to the lactating mammary gland of a transgenic mammal.

Example 5
Testing and Characterization of Gene Constructs in Transgenic Mice Transgene constructs are generally tested in a mouse model system to assess their ability to direct high levels of expression and their ability to express in a tissue-specific manner. Transgenic mice were generated with the expression of EPOa-hSA fusions targeted to the mammary gland.

Transgenic mice were generated by microinjecting mouse embryos with fusion protein encoding DNA constructs. Western analysis of the milk of the EPOa-hSA fusion protein transgenic mice was performed using monoclonal anti-EPO or anti-hSA antibodies to determine which animals express EPOa-hSA fusion protein in the milk. The level of EPOa-hSA fusion protein detected ranged from about 0.2 mg/ml to 4 mg/ml.

Example 6
Bioactivity of EPOa-hSA in Transgenic Mice

The bioactivity of the EPOa-hSA fusion protein was analyzed by determining changes in hematocrit levels of transgenic mice expressing EPOa-hSA fusion protein. See Table 1. Hematocrit levels of the transgenic mice (655-1-8, 655-1-16, 655-1-43) were compared to levels in control mice (the CD1mice). Normal hematocrit levels are about 50.

TABLE 1

TRANSGENIC MICE EXPRESSING EPOA-HSA FUSION PROTEIN

| Mouse | d.p.partum | Hematocrit | Status (October 1998) |
|---|---|---|---|
| 655-1-8 | 17 | 90 | Died July 1998 |
| 655-1-16 | 16 | 86 | Died August 1998 |
| 655-1-43 | 17 | 93 | Alive |
| CD1 | 17 | 50 | NA |
| CD1 | 17 | 57 | NA |
| CD1 | 17 | 52 | NA |

As shown in Table I, expression of the EPOa-hSA fusion protein in transgenic mice significantly increased hematocrit levels in the mice.

In addition, Table II provides the hematocrit levels of virgin offspring of the founder transgenic mice and hematocrit levels for founder males (678-1-11 and 678-1-23) to demonstrate the expression of EPOa-hSA and the bioactivity of EPOa-hSA in these mice.

TABLE II

HEMATOCRIT LEVELS IN VIRGIN OFFSPRING OF TRANSGENIC FOUNDER MICE EXPRESSING EPOa-hSA FUSION PROTEIN

| Mouse | Founder | Hematocrit | Status (October 1998) |
|---|---|---|---|
| 655-2-160 | 56 (low) | 50 | Alive |
| 655-2-165 | 57 (high) | 91 | Alive |
| 655-2-147 | 23 (male) | 86 | Alive |
| 678-2-155 | 31 (n.d./low) | 43 | Alive |
| 678-1-11 | (male) | 83 | Alive |
| 678-1-23 | (male) | 79 | Alive |

The hematocrit levels of the offspring provide basal levels of expression of EPOa-hSA under the control of a casein promoter. As shown in Table II, even low expression levels of EPOa-hSA fusion protein have a significant in vivo effect.

Example 7

Generation and Characterization of Transgenic Goats

The sections outlined below briefly describe the major steps in the production of transgenic goats.

Goat Species and Breeds:

Swiss-origin goats, e.g., the Alpine, Saanen, and Toggenburg breeds, are preferred in the production of transgenic goats.

Goat Superovulation:

The timing of estrus in the donors is synchronized on Day 0 by 6 mg subcutaneous norgestomet ear implants (Syncromate-B, CEVA Laboratories, Inc., Overland Park, Kans.). Prostaglandin is administered after the first seven to nine days to shut down the endogenous synthesis of progesterone. Starting on Day 13 after insertion of the implant, a total of 18 mg of follicle-stimulating hormone (FSH—Schering Corp., Kenilworth, N.J.) is given intramuscularly over three days in twice-daily injections. The implant is removed on Day 14. Twenty-four hours following implant removal the donor animals are mated several times to fertile males over a two-day period (Selgrath, et al., Theriogenology, 1990. pp. 1195–1205).

Embro Collection:

Surgery for embryo collection occurs on the second day following breeding (or 72 hours following implant removal). Superovulated does are removed from food and water 36 hours prior to surgery. Does are administered 0.8 mg/kg Diazepam (Valium®) IV, followed immediately by 5.0 mg/kg Ketamine (Keteset), IV. Halothane (2.5%) is administered during surgery in 2 L/min oxygen via an endotracheal tube. The reproductive tract is exteriorized through a midline laparotomy incision. Corpora lutea, unruptured follicles greater than 6 mm in diameter, and ovarian cysts are counted to evaluate superovulation results and to predict the number of embryos that should be collected by oviductal flushing. A cannula is placed in the ostium of the oviduct and held in place with a single temporary ligature of 3.0 Prolene. A 20 gauge needle is placed in the uterus approximately 0.5 cm from the uterotubal junction. Ten to twenty ml of sterile phosphate buffered saline (PBS) is flushed through the cannulated oviduct and collected in a Petri dish. This procedure is repeated on the opposite side and then the reproductive tract is replaced in the abdomen. Before closure, 10–20 ml of a sterile saline glycerol solution is poured into the abdominal cavity to prevent adhesions. The linea alba is closed with simple interrupted sutures of 2.0 Polydioxanone or Supramid and the skin closed with sterile wound clips.

Fertilized goat eggs are collected from the PBS oviductal flushings on a stereomicroscope, and are then washed in Ham's F12 medium (Sigma, St. Louis, Mo.) containing 10% fetal bovine serum (FBS) purchased from Sigma. In cases where the pronuclei are visible, the embryos is immediately microinjected. If pronuclei are not visible, the embryos can be placed in Ham's F12 containing 10% FBS for short term culture at 37° C. in a humidified gas chamber containing 5% $CO_2$ in air until the pronuclei become visible (Selgrath, et al., Theriogenology, 1990. pp. 1195–1205).

Microinjection Procedure:

One-cell goat embryos are placed in a microdrop of medium under oil on a glass depression slide. Fertilized eggs having two visible pronuclei are immobilized on a flame-polished holding micropipet on a Zeiss upright microscope with a fixed stage using Normarski optics. A pronucleus is microinjected with the DNA construct of interest, e.g., a BC355 vector containing the human erythropoietin analog-human serum albumin (EPOa-hSA) fusion protein gene operably linked to the regulatory elements of the goat beta-casein gene, in injection buffer (Tris-EDTA) using a fine glass microneedle (Selgrath, et al., Theriogenology, 1990. pp. 1195–1205).

Embryo Development:

After microinjection, the surviving embryos are placed in a culture of Ham's F12 containing 10% FBS and then incubated in a humidified gas chamber containing 5% $CO_2$ in air at 37° C. until the recipient animals are prepared for embryo transfer (Selgrath, et al., Theriogenology, 1990. p. 1195–1205).

Preparation of Recipients:

Estrus synchronization in recipient animals is induced by 6 mg norgestomet ear implants (Syncromate-B). On Day 13 after insertion of the implant, the animals are given a single non-superovulatory injection (400 I.U.) of pregnant mares serum gonadotropin (PMSG) obtained from Sigma. Recipient females are mated to vasectomized males to ensure estrus synchrony (Selgrath, et al., Theriogenology, 1990. pp. 1195–1205).

Embryo Transfer:

All embryos from one donor female are kept together and transferred to a single recipient when possible. The surgical procedure is identical to that outlined for embryo collection outlined above, except that the oviduct is not cannulated, and the embryos are transferred in a minimal volume of Ham's F12 containing 10% FBS into the oviductal lumen via the fimbria using a glass micropipet. Animals having more than six to eight ovulation points on the ovary are deemed unsuitable as recipients. Incision closure and post-operative care are the same as for donor animals (see, e.g., Selgrath, et al., Theriogenology, 1990. pp. 1195–1205).

Monitoring of Pregnancy and Parturition:

Pregnancy is determined by ultrasonography 45 days after the first day of standing estrus. At Day 110 a second ultrasound exam is conducted to confirm pregnancy and assess fetal stress. At Day 130 the pregnant recipient doe is vaccinated with tetanus toxoid and Clostridium C&D. Selenium and vitamin E (Bo-Se) are given IM and Ivermectin was given SC. The does are moved to a clean stall on Day 145 and allowed to acclimatize to this environment prior to inducing labor on about Day 147. Parturition is induced at Day 147 with 40 mg of PGF2a (Lutalyse®, Upjohn Company, Kalamazoo, Mich.). This injection is given IM in two doses, one 20 mg dose followed by a 20 mg dose four hours later. The doe is under periodic observation during the day and evening following the first injection of Lutalyse® on Day 147. Observations are increased to every 30 minutes beginning on the morning of the second day. Parturition occurred between 30 and 40 hours after the first injection. Following delivery the doe is milked to collect the colostrum and passage of the placenta is confirmed.

Verification of the Transgenic Nature of $F_0$ Animals:

To screen for transgenic $F_0$ animals, genomic DNA is isolated from two different cell lines to avoid missing any mosaic transgenics. A mosaic animal is defined as any goat that does not have at least one copy of the transgene in every cell. Therefore, an ear tissue sample (mesoderm) and blood sample are taken from a two day old $F_0$ animal for the isolation of genomic DNA (Lacy, et al., A Laboratory Manual, 1986, Cold Springs Harbor, NY; and Herrmann and Frischauf, Methods Enzymology, 1987. 152: pp. 180–183). The DNA samples are analyzed by the polymerase chain reaction (Gould, et al., Proc. Natl. Acad. Sci, 1989. 86: pp. 1934–1938) using primers specific for human EPOa-hSA fusion protein gene and by Southern blot analysis (Thomas, Proc Natl. Acad. Sci., 1980. 77:5201–5205) using a random primed EPO or hSA cDNA probe (Feinberg and Vogelstein, *Anal Bioc.*, 1983. 132: pp. 6–13). Assay sensitivity is estimated to be the detection of one copy of the transgene in 10% of the somatic cells.

Generation and Selection of Production Herd

The procedures described above can be used for production of transgenic founder ($F_0$) goats, as well as other transgenic goats. The transgenic $F_0$ founder goats, for example, are bred to produce milk, if female, or to produce a transgenic female offspring if it is a male founder. This transgenic founder male, can be bred to non-transgenic females, to produce transgenic female offspring.

Transmission of Transgene and Pertinent Characteristics

Transmission of the transgene of interest, in the goat line is analyzed in ear tissue and blood by PCR and Southern blot analysis. For example, Southern blot analysis of the founder male and the three transgenic offspring shows no rearrangement or change in the copy number between generations. The Southern blots are probed with human EPOa-hSA fusion protein CDNA probe. The blots are analyzed on a Betascope 603 and copy number determined by comparison of the transgene to the goat beta casein endogenous gene.

Evaluation of Expression Levels

The expression level of the transgenic protein, in the milk of transgenic animals, is determined using enzymatic assays or Western blots.

Other embodiments are within the following claims.

What is claimed is:

1. An isolated nucleic acid comprising a nucleotide sequence which encodes an erythropoietin analog-human serum albumin (EPOa-hSA) fusion protein, wherein each of amino acid resdues 24, 38, 83 and 126 of human erythropoietin (EPO) has been altered such that it does not serve as a glycosylation site in the EPOa.

2. An expression vector or construct which comprises the nucleic acid of claim 1.

3. A cell which comprises the vector or construct of claim 2.

4. The vector of claim 2, further comprising a promoter.

5. The vector of claim 4, wherein the promoter is a promoter which directs expression in a tissue specific manner.

6. The vector of claim 4, wherein the promoter is a promoter which directs expression in mammary epithelial cells.

7. The nucleic acid of claim 1, wherein the encoded EPOa-hSA has the formula:

R1-L-R2; R2-L-R1; or R1-L-R2-L-R1, wherein R1 is an erythropoietin analog amino acid sequence; L is a peptide linker and R2 is human serum albumin amino acid sequence.

8. The nucleic acid of claim 1, wherein at least one amino acid residue of the encoded EPOa-hSA which can serve as a glycosylation site in EPO has been deleted.

9. The nucleic acid of claim 1, wherein at least one amino acid residue of the encoded EPOa-hSA which can serve as a glycosylation site in EPO has been replaced with an amino acid which does not serve as a site for glycosylation.

10. The nucleic acid of claim 9, wherein the amino acid residue which is replaced is an N-linked glycosylation site of EPO.

11. The nucleic acid of claim 10, wherein the N-linked glycosylation site is altered by replacing an amino acid residue Asn with Gln.

12. The nucleic acid of claim 10, wherein amino acid residue 24 of human EPO has been replaced with Gln.

13. The nucleic acid of claim 10, wherein amino acid residue 38 of human EPO has been replaced with Gln.

14. The nucleic acid of claim 10, wherein amino acid residue 83 of human EPO has been replaced with Gln.

15. The nucleic acid of claim 9, wherein the amino acid residue which is replaced is an O-linked glycosylation site of EPO.

16. The nucleic acid of claim 15, wherein the O-linked glycosylation site is altered by replacing an amino acid residue Ser with Ala.

17. The nucleic acid of claim 15, wherein amino acid residue 126 of human EPO has been replaced with Ala.

18. The nucleic acid of claim 9, wherein amino acid residues 24 of human EPO is replaced with a Gln, amino acid residues 38 of human EPO is replaced with a Gln, amino acid residue 83 of human EPO is replaced with a Gln and amino acid residue 126 of human EPO have been replaced with an Ala.

19. An isolated nucleic acid comprising a nucleotide sequence which encodes an erythropoietin analog-human serum albumin (EPOa-hSA) fusion protein, wherein sequence in which a nucleic acid which comprises a nucleotide sequence encoding an EPOa is operably linked to a nucleic acid which comprises a nucleotide sequence encoding human serum albumin, wherein each of amino acid residues 24, 38, 83 and 126 of human erythropoietin (EPO) has been altered such that it does not serve as a glycosylation site in the EPOa.

20. The method of claim 19, wherein said cell is selected from a group consisting of a mammalian, yeast, plant, insect or a bacterial cell.

21. A method for making an EPOa-hSA fusion protein comprising:

supplying a cell of claim 3 which comprises a nucleic acid which encodes an EPOa-hSA fusion protein and expressing said EPOa-hSA fusion protein from said nucleic acid, thereby making said EPOa-hSA fusion protein.

22. A method for making an EPOa-hSA fusion protein in a cultured cell comprising supplying a cell which includes a nucleic acid of claim 1, and expressing the EPOa-hSA fusion protein from the nucleic acid, thereby making the EPOa-hSA fusion protein.

* * * * *

UNITED STATES PATENT AND TRADEMARK OFFICE
CERTIFICATE OF CORRECTION

| | | |
|---|---|---|
| PATENT NO. | : 6,548,653 B1 | Page 1 of 1 |
| APPLICATION NO. | : 09/333213 | |
| DATED | : April 15, 2003 | |
| INVENTOR(S) | : Michael Young et al. | |

It is certified that error appears in the above-identified patent and that said Letters Patent is hereby corrected as shown below:

In column 1, line 5, please delete "filed Jun. 15, 1999." and insert -- filed Jun. 15, 1998.--

Signed and Sealed this

Twenty-fourth Day of October, 2006

JON W. DUDAS
*Director of the United States Patent and Trademark Office*

SEQUENCE LISTING

```
<160> NUMBER OF SEQ ID NOS: 4

<210> SEQ ID NO 1
<211> LENGTH: 40
<212> TYPE: PRT
<213> ORGANISM: Artificial Sequence
<220> FEATURE:
<223> OTHER INFORMATION: Synthetically generated linker sequence;
      subsets 2 through 8 (each consisting of a repetition of the
      first five amino acids) encompassing
      positions 6 through 40 may be absent or present

<400> SEQUENCE: 1

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly
        35                  40

<210> SEQ ID NO 2
<211> LENGTH: 11
<212> TYPE: PRT
<213> ORGANISM: Artificial Sequence
<220> FEATURE:
<223> OTHER INFORMATION: Synthetically generated linker sequence

<400> SEQUENCE: 2

Gly Gly Gly Gly Ser Gly Gly Gly Gly Ser
1               5                   10

<210> SEQ ID NO 3
<211> LENGTH: 20
<212> TYPE: PRT
<213> ORGANISM: Artificial Sequence
<220> FEATURE:
<223> OTHER INFORMATION: Synthetically generated linker sequence

<400> SEQUENCE: 3

Ser Gly Gly Gly Gly Ser Gly Gly Gly Gly Ser Gly Gly Gly Gly Ser
```

```
                1               5                   10                  15
Gly Gly Gly Gly
                                20

<210> SEQ ID NO 4
<211> LENGTH: 17
<212> TYPE: PRT
<213> ORGANISM: Artificial Sequence
<220> FEATURE:
<223> OTHER INFORMATION: Synthetically generated linker sequence

<400> SEQUENCE: 4

Ser Ser Ser Ser Gly Ser Ser Ser Ser Gly Ser Ser Ser Ser Gly Ser
 1               5                   10                  15

Pro
```